(12) United States Patent
Dimitrov et al.

(10) Patent No.: US 10,647,754 B2
(45) Date of Patent: May 12, 2020

(54) STABILIZED SINGLE HUMAN CD4 DOMAINS AND FUSION PROTEINS

(71) Applicant: The United States of America, as represented by the Secretary, Department of Health and Human Services, Bethesda, MD (US)

(72) Inventors: Dimiter S. Dimitrov, Frederick, MD (US); Weizao Chen, Frederick, MD (US); Prabakaran Ponraj, Frederick, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/784,988

(22) Filed: Oct. 16, 2017

(65) Prior Publication Data

US 2018/0086812 A1 Mar. 29, 2018

Related U.S. Application Data

(62) Division of application No. 14/777,245, filed as application No. PCT/US2014/024120 on Mar. 12, 2014, now abandoned.

(60) Provisional application No. 61/791,885, filed on Mar. 15, 2013.

(51) Int. Cl.
| | | |
|---|---|---|
| *C07K 14/73* | (2006.01) | |
| *A61K 38/16* | (2006.01) | |
| *A61K 38/17* | (2006.01) | |
| *C07K 16/10* | (2006.01) | |
| *A61K 47/64* | (2017.01) | |
| *A61K 38/00* | (2006.01) | |

(52) U.S. Cl.
CPC ...... *C07K 14/70514* (2013.01); *A61K 38/162* (2013.01); *A61K 38/1774* (2013.01); *A61K 47/6425* (2017.08); *C07K 16/1063* (2013.01); *A61K 38/00* (2013.01); *C07K 2319/00* (2013.01); *C07K 2319/30* (2013.01); *C07K 2319/33* (2013.01)

(58) Field of Classification Search
CPC .......... C07K 14/70514; C07K 16/1063; C07K 2319/30; C07K 2319/00; A61K 47/6425; A61K 38/1774
See application file for complete search history.

(56) References Cited

U.S. PATENT DOCUMENTS

8,911,728 B2 12/2014 Dimitrov et al.
2004/0137000 A1 7/2004 Shugene et al.

FOREIGN PATENT DOCUMENTS

| CN | 1738646 A | 2/2006 | |
|---|---|---|---|
| CN | 102649818 A | 8/2012 | |
| WO | WO 89/03222 | 4/1989 | |
| WO | WO 2011/146891 A2 * | 11/2011 | ............. C07K 16/10 |
| WO | WO 2016/153572 A1 | 9/2016 | |

OTHER PUBLICATIONS

Chen et al., "Bifunctional fusion proteins of the human engineered antibody domain m36 with human soluble CD4 are potent inhibitors of diverse HIV-1 isolates," *Antiviral Res.*, 88 (1), 107-115 (2010).
Chen et al., "Engineered single human CD4 domains as potent HIV-1 inhibitors and components of vaccine immunogens," *J. Viral.*, 85 (18), 9395-9405 (2011).
Chen et al., "Human domain antibodies to conserved sterically restricted regions on gp120 as exceptionally potent cross-reactive HIV-1 neutralizers," *Proc. Natl. Acad. Sci. U.S.A.*, 105 (44), 17121-17126 (2008).
Dalgleish et al., "The CD4 (T4) antigen is an essential component of the receptor for the AIDS retrovirus," *Nature*, 312 (5996), 763-767 (1984).
Deen et al., "A soluble form of CD4 (T4) protein inhibits AIDS virus infection," *Nature*, 331 (6), 82-84 (1988).
Germain, "T-cell signaling: the importance of receptor clustering," *Curr. Biol.*, 7 (10), R640-R644 (1997).
Kwong et al., "Structure of HIV gp120 envelope glycoprotein in complex with the CD4 receptor and a neutralizing human antibody," *Nature*, 393 (6686), 648-659 (1998).
Lagenaur et al., "sCD4-17b bifunctional protein: etremely broad and potent neutralization of HIV-1 Env pseudotyped viruses from genetically diverse primary isolates," *Retrovirology*, 7 (11), 1-13 (2010).
Moebius et al., "The human immunodeficiency virus gp120 binding site on CD4: delineation by quantitative equilibrium and kinetic binding studies of mutants in conjunction with a high-resolution CD4 atomic structure," *J. Exp. Med.*, 176 (2), 507-517 (1992).
Moebius et al., "Delineation of an extended surface contact area on human CD4 involved in class II major histocompatibility complex binding," *Proc. Natl. Acad. Sci. USA*, 90 (17), 8259-8263 (1993).
Ryu et al., "Crystal structure of an HIV-binging recombinant fragment of human CD4," *Nature*, 348 (6300), 419-429 (1990).
Saha et al., "Design and characterization of stabilized derivatives of human CD4D12 and CD4D1," *Biochemistry*, 50 (37), 7891-7900 (2011).
Sakihama et al., "Oligomerization of CD4 is required for stable binding to class II major histocompatibility complex proteins but not for interaction with human immunodeficiency virus gp120," *Proc. Natl. Acad. Sci. USA*, 92 (14), 6444-6448 (1995).
Sharma et al., "Protein minimization of the gp120 binding region of human CD4," *Biochemistry*, 44 (49), 16192-16202 (2005).
Traunecker et al., "Soluble CD4 molecules neutralize human immunodeficiency virus type 1," *Nature*, 331 (6151), 84-86 (1988).

(Continued)

*Primary Examiner* — Jeffrey S Parkin
(74) *Attorney, Agent, or Firm* — Leydig, Voit & Mayer, Ltd.

(57) ABSTRACT

The invention provides a polypeptide comprising a single domain CD4, as well as a fusion protein comprising the single domain CD4 and one or more fusion partners. A nucleic acid encoding the polypeptide or fusion protein, as well as compositions or cells comprising the polypeptide, fusion protein, or nucleic acid also are provided.

18 Claims, 12 Drawing Sheets

Specification includes a Sequence Listing.

(56) References Cited

OTHER PUBLICATIONS

Wang et al., "Crystal structure of the human CD4 N-terminal two-domain fragment complexed to a class II MHC molecule," *Proc. Nati. Acad. Sci. USA*, 98 (19), 10799-10804 (2001).
Wu et al., "Dimeric association and segmental variability in the structure of human CD4," *Nature*, 387 (6632), 527-530 (1997).
European Patent Office, International Search Report isssued in PCT/US2014/024120, dated Sep. 19, 2014, 6 pages.
European Patent Office, Written Opinion of the International Searching Authority, issued in PCT/US2014/024120, 8 pages.
The International Bureau of WIPO, International Preliminary Report on Patentability, issued in PCT/US2014/024120, 9 pages.
U.S. Appl. No. 14/777,245, filed Sep. 15, 2015.
U.S. Appl. No. 15/561,268, filed Sep. 25, 2017.
U.S. Appl. No. 13/699,535, filed Jan. 11, 2013.

\* cited by examiner

FIGURE 1

| | | | | | | | | | | SEQ ID NO: |
|---|---|---|---|---|---|---|---|---|---|---|
| | 1 | 10 | 20 | 30 | 40 | 50 | 60 | 70 | 80 | 90 | 100 | |
| D1 | KKVVLGKKGDTVELTCTASQKKSIQFHWKNSNQIKILGNQGSFLTKGPSKLNDRADSRRSLWDQGNFPLIIKNLKIEDSDTYICEVEDQKEEVQLLVFG | 3 |
| mD1.2 | ....Y...............N.......................................................... | 4 |
| mD1.22 | ....Y...............N..............................V..........P................ | 1 |
| mD1.23 | ....Y...............N......D.......................................P...........V.V. | 2 |

STABILIZED SINGLE HUMAN CD4 DOMAINS AND FUSION PROTEINS

CROSS-REFERENCE TO RELATED APPLICATIONS

This patent application is a divisional application of U.S. patent application Ser. No. 14/777,245, filed on Sep. 15, 2015, which is the U.S. National Phase of International Patent Application No. PCT/US2014/024120, filed on Mar. 12, 2014, which claims the benefit of U.S. Provisional Patent Application No. 61/791,885, filed on Mar. 15, 2013, each of which is incorporated by reference.

STATEMENT REGARDING FEDERALLY SPONSORED RESEARCH AND DEVELOPMENT

This invention was made with Government support under project number ZIA BC 011155 by the National Institutes of Health, National Cancer Institute. The Government has certain rights in the invention.

SEQUENCE LISTING

Incorporated by reference in its entirety herein is a nucleotide/amino acid sequence listing submitted concurrently herewith and identified as follows: One 41,509 Byte ASCII (Text) file named "735874 ST25.TXT," created Oct. 13, 2017.

BACKGROUND OF THE INVENTION

CD4 is a nonpolymophic transmembrane glycoprotein expressed on the surface of most thymocytes and a sub-population of matured T cells (CD4$^+$ T cells) (see Germain, *Curr. Biol.*, 7: R640-R644 (1997)). It is composed of four immunoglobulin-like extracellular domains, a transmembrane segment and a cytoplasmic tail non-covalently associated with a src-family tyrosine kinase, Lck. As an important component of the immune system, CD4 functions as a co-receptor assisting the T cell receptor (TCR) on the CD4$^+$ T cells for stronger association with class II major histocompatibility complex (MHCII) on antigen-presenting cells (APCs). The association is sufficient to trigger T-cell signaling transduction resulting in activation of the CD4$^+$ T cells.

CD4 also contributes directly to the signal transduction by driving signaling cascade through its kinase-linked cytoplasmic tail. The crystal structure of human CD4-murine MHCII shows that only the first extracellular domain (D1) of CD4 makes contact with MHCII (see Wang et al., *Proc. Natl. Acad. Sci. USA*, 98: 10799-10804 (2001)). However, mutational analysis indicates that in addition to D1, other domains also affect binding to MHCII (see Moebius et al., *Proc. Natl. Acad. Sci. USA*, 90: 8259-8263 (1993)). Moreover, oligomerization of CD4 is required for stable interaction with MHCII and efficient T-cell activation (see Sakihama et al., *Proc. Natl. Acad. Sci. USA*, 92: 6444-6448 (1995)).

CD4 is also the primary receptor for HIV-1 (see Dalgleish et al., *Nature*, 312: 763-767 (1984)). HIV-1 entry is initiated by binding of the viral envelope glycoprotein (Env) gp120 to cellular receptor CD4. The interaction results in extensive conformational rearrangements of gp120 and subsequently gp41 after engagement of a coreceptor (either CCR5 or CXCR4). The structural rearrangements of Envs and the interplay between Envs and the cellular receptor and co-receptor bring viral membrane toward target cell membrane, and eventually cause membrane fusion and viral entry. Because CD4 plays a key role in HIV-1 infection, recombinant solubly expressed CD4 (sCD4) containing either all four (T4) (see Deen et al., *Nature*, 331: 82-84 (1988)) or the first two extracellular domains (D1D2) (see Traunecker et al., *Nature*, 331: 84-86 (1988)) is a potent inhibitor of HIV-1 entry and used for crystallization alone (see Wu et al., *Nature*, 387: 527-530 (1997) and Ryu et al., *Nature*, 348: 419-429 (1990)) or with gp120 (see Kwong et al., *Nature*, 393: 648-659 (1998)).

In Sharma et al. (*Biochemistry*, 44: 16192-16202 (2005)), D1 was generated by using a mutational strategy and purified from the sonication supernatant of *E. coli*. However, the purified protein was stable only at low pH (4.0) and partially improperly folded, and had affinity several-fold lower than that of D1D2 or T4.

In Chen et al. (*J. Virol.*, 85: 9395-9405 (2011)), two stable monomeric D1 mutants, mD1.1 and mD1.2 were identified, which were significantly more soluble and bound Env gp120s more strongly (50-fold) than D1D2, neutralized a panel of HIV-1 primary isolates from different clades more potently than D1D2, induced conformation changes in gp120, and sensitized HIV-1 for neutralization by CD4-induced antibodies.

However, the desire for new D1s that are correctly folded, highly soluble and stable under physiological conditions while preserving not only binding activity and specificity but also other functions, such as induction of conformational changes in HIV-1 gp120, remains.

BRIEF SUMMARY OF THE INVENTION

The invention provides a polypeptide comprising a single domain CD4, such as SEQ ID NO: 1 or SEQ ID NO: 2, as well as a fusion protein comprising the single domain CD4 and one or more fusion partners, wherein the one or more fusion partners optionally is joined to the single domain CD4 via a linker. Additionally, constructs comprising multivalent fusion proteins are provided. Nucleic acids encoding the single domain CD4 and fusion proteins, as well as compositions or cells comprising the single domain CD4, fusion proteins, constructs, or nucleic acids, also are provided.

The invention also provides a method of inhibiting an HIV infection in a cell or a host comprising administering the polypeptide, fusion protein, or construct to the cell or host, such that the HIV infection is inhibited.

BRIEF DESCRIPTION OF THE SEVERAL VIEWS OF THE DRAWINGS

FIG. 1 is an amino acid sequence comparison between human single domain CD4 (D1) and mutants thereof.

In FIG. 5A, [θ](103 deg cm$^2$ dmol$^{-1}$) is indicated on the y-axis and wavelength (nm) is indicated on the x-axis. In FIG. 5B, the fraction folded (as assayed by circular dichroism) is indicated on the y-axis and temperature (° C.) is indicated on the x-axis.

DETAILED DESCRIPTION OF THE INVENTION

Figure 2:
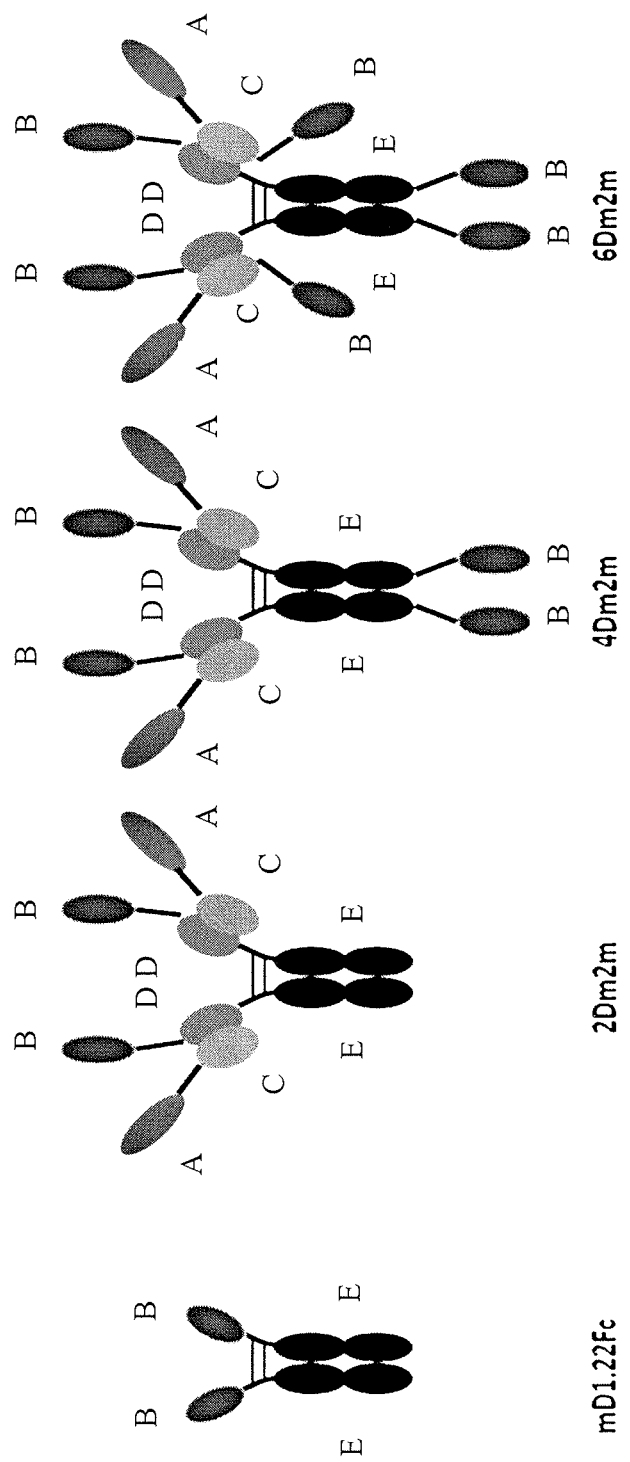
FIG. 2 is a depiction of constructs containing multiple fusion proteins, wherein A denotes an antibody or antibody fragment (e.g., m36.4), B denotes a single domain CD4 (e.g., the inventive polypeptide), C denotes a light chain constant region, D denotes a heavy chain constant region, and E denotes an Fc region or portion thereof. Straight lines connecting the regions denote linker sequences. The line represents optional bonds.

The invention provides a single domain CD4 that has the binding activity and specificity of full-length CD4 and maintains other functions, such as induction of conformational changes in HIV-1 gp120. Due to decreased molecular size, the single domain CD4 has excellent biological properties including improved binding kinetics, soluble expression in *E. coli*, higher solubility, stability and specificity, minimization of immunogenicity in animals, and better penetration into tissues, such as the densely packed lymphoid environments (e.g., spleen, lymph node and gut) where HIV-1 mostly replicates and spreads.

The inventive single domain CD4 comprises, consists essentially of, or consists of the amino acid sequence of SEQ ID NO: 1 or SEQ ID NO: 2. The invention also provides a polypeptide comprising variants of SEQ ID NO: 1 or SEQ ID NO: 2 with up to 20 (e.g., 0, 1, 2, 3, 4, 5, 6, 7, 8, 9, 10, 11, 12, 13, 14, 15, 16, 17, 18, 19, or 20) additions, deletions, substitutions, or insertions. Preferably, the invention provides a polypeptide comprising SEQ ID NO: 1 or SEQ ID NO: 2 with up to 10 additions, deletions, substitutions, or insertions, wherein the polypeptide does not comprise SEQ ID NO: 4.

The inventive polypeptide preferably is a recombinant or synthetic polypeptide, which is non-naturally occurring.

The inventive polypeptide can be provided alone, or as part of a fusion protein comprising the polypeptide and one or more fusion partners. The fusion partner can be any suitable moiety that does not substantially inhibit the polypeptide's ability to bind its target. Desirably, the fusion partner enhances the stability and/or potency of the polypeptide as compared to the stability or potency of the polypeptide in the absence of the fusion partner. For instance, the fusion partner can be a naturally occurring protein or fragment thereof that resists degradation or removal by endogenous mechanisms in vivo, thereby increasing the half-life of the fusion protein as compared to the polypeptide in the absence of the fusion protein.

Examples of suitable fusion partners include: (a) proteins from the extracellular matrix, such as collagen, laminin, integrin, and fibronectin; (b) proteins found in blood, such as serum albumin, serum albumin-binding peptide (SAbp), fibrinogen A, fibrinogen B, serum amyloid protein A, heptaglobin, protein, ubiquitin, uteroglobulin, β-2 microglobulin, plasminogen, lysozyme, cystatin C, α-1-antitrypsin, and pancreatic kypsin inhibitor; (c) immune serum proteins, such as IgE, IgG, IgM, and their fragments (e.g., Fc); (d) transport proteins, such as retinol binding protein; (e) defensins, such as β-defensin 1, neutrophil defensins 1, 2 and 3; (f) proteins found at the blood brain barrier or in neural tissues, such as melanocortin receptor, myelin, ascorbate transporter; (g) transferrin receptor specific ligand-neuropharmceutical agent fusion proteins, brain capillary endothelial cell receptor, transferrin, transferrin receptor, insulin, insulin-like growth factor 1 (IGF 1) receptor, insulin-like growth factor 2 (IGF 2) receptor, insulin receptor; (h) proteins localized to the kidney, such as polycystin, type IV collagen, organic anion transporter K1, Heymann's antigen; (i) proteins localized to the liver, such as alcohol dehydrogenase, G250; (j) blood coagulation factor X; (k) α-1 antitrypsin; (l) HNF 1 α; (m) proteins localized to the lung, such as secretory component; (n) proteins localized to the heart, such as HSP 27; (o) proteins localized to the skin, such as keratin; (p) bone specific proteins, such as bone morphogenic proteins (BMPs), for example, BMP-2, -4, -5, -6, -7 (also referred to as osteogenic protein (OP-1) and -8 (OP-2); (q) tumor specific proteins, such as human trophoblast antigen, herceptin receptor, estrogen receptor, cathepsins, for example, cathepsin B (found in liver and spleen); (r) disease-specific proteins, such as antigens expressed only on activated T-cells: including LAG-3 (lymphocyte activation gene); osteoprotegerin ligand (OPGL); OX40; metalloproteases, including CG6512 Drosophila, human paraplegin, human FtsH, human AFG3L2, murine ftsH; angiogenic growth factors, including acidic fibroblast growth factor (FGF-I), basic fibroblast growth factor (FGF-2), Vascular endothelial growth factor/vascular permeability factor (VEGFNPF), transforming growth factor-α (TGF-α), tumor necrosis factor-alpha (TNF-α), angiogenin, interleukin-3 (IL-3), interleukin-8 (IL-8), platelet derived endothelial growth factor (PD-ECGF), placental growth factor (PIGF), midkine platelet-derived growth factor-BB (PDGF), fractalkine; (s) stress proteins (heat shock proteins); and (t) proteins involved in Fc transport. Additional fusion partners for use in connection herewith are described in WO 2009/089295.

In one embodiment, the fusion partner is an immunoglobulin Fc region or portion thereof (e.g., the CH2 or CH3 region), especially the Fc region of a human immunoglobulin, such as a human IgG1 Fc region. Examples of an Fc region or portion thereof for use in the invention include, but are not limited to, the amino acid sequence of SEQ ID NO: 7 and SEQ ID NO: 8.

In another embodiment, the fusion partner is an antibody or antibody fragment (e.g., Fab, scFv, dAb, etc.). Preferably, the antibody is a single-domain antibody (a.k.a. "domain antibody ("dAb") or "engineered antibody domain" ("eAd")), which is an antibody fragment consisting of a single monomeric variable antibody domain from the heavy or light chains. For example, the eAd can comprise SEQ ID NO: 12, SEQ ID NO: 13, SEQ ID NO: 14, SEQ ID NO: 15, or SEQ ID NO: 16, also referenced herein as the m36, m36.1, m36.2, m36.4, or m36.5 antibodies, respectively.

In another embodiment, the fusion partner is an HIV (e.g., HIV-1 or HIV-2) envelope glycoprotein. Examples of the HIV envelope glycoprotein include gp120 and gp140. Preferably, the HIV envelope glycoprotein is HIV-1 gp120.

The fusion protein comprises one or more fusion partners (e.g., two, three, four, five, or more fusion partners). For instance, the fusion protein can comprise the inventive polypeptide, an eAd (e.g., the m36, m36.1, m36.2, m36.4, or m36.5 antibodies of SEQ ID NOs: 12-16, respectively) and a stability-enhancing fusion partner, such as an immunoglobulin Fe region (e.g., human IgG1 Fe) or portion thereof (e.g., CH3).

The inventive polypeptide and one or more fusion partners can be joined via a linker (i.e., a flexible molecular connection, such as a flexible polypeptide chain). The linker can be any suitable linker of any length, but is preferably at least about 15 (e.g., at least about 20, at least about 25, at least about 30, at least about 35, at least about 40, at least about 45, at least about 50, or ranges thereof) amino acids in length. In one embodiment, the linker is an amino acid sequence that is naturally present in immunoglobulin molecules of the host, such that the presence of the linker would not result in an immune response against the linker sequence by the mammal. Examples of suitable linkers include, but are not limited to, linkers that comprise one or more (e.g., two, three, four, five, six, seven, eight, nine, or ten) GIS motifs, such as the linkers of SEQ ID NOs: 9-11.

By way of further illustration, examples of fusion proteins according to the invention can have the following configuration: (first fusion partner)-(optional first linker)-(inventive polypeptide (referred to as mD1))-(optional second linker)-(optional second fusion partner). More specific illustrative examples include the following: mD1-Fc (SEQ ID NO: 17), gp120-linker-mD1, eAd-linker-mD1, mD1-linker-CH3, eAd-linker-mD1-linker-CH3, and eAd-linker-mD1-Fc.

The invention also provides a fusion protein comprising:

A-(optional linker)-C-(optional linker)-B  (Formula (I))

or

B-(optional linker)-D-(optional linker)-E-(optional linker)-B  (Formula (II))

wherein A denotes an antibody or antibody fragment (e.g., Fab, scFv, eAd, etc.), B denotes the inventive polypeptide (SEQ ID NO: 1 or SEQ ID NO: 2; referred to as mD1), C denotes an immunoglobulin light chain constant region (e.g., human IgG1 kappa light chain constant region), D denotes an immunoglobulin heavy chain constant region (e.g., human IgG1 heavy chain constant region), and E denotes an Fe region or a portion thereof (e.g., the Fe region from human IgG1). Specific examples include mD1.22-linker-human IgG1 heavy chain constant region-linker-mD1 and 36.4 eAd-linker-human IgG1 light chain constant region-linker-mD1.22.

Two or more of the fusion proteins can be conjugated or otherwise joined in a larger construct. For instance, two fusion proteins of Formula (I) above and two fusion proteins of Formula (II) above can be assembled into a single construct, as depicted in FIG. 2 (6Dm2m). In one embodiment, the fusion protein of Formula (I) comprises SEQ ID NO: 23 and the fusion protein of Formula (II) comprises SEQ ID NO: 22.

Alternatively, two fusion proteins of Formula (II) above and two fusion proteins of A-(optional linker)-C (Formula III) can be assembled into a single construct, as depicted in FIG. 2 (4Dm2m). In one embodiment, the fusion protein of Formula (III) comprises SEQ ID NO: 21 and the fusion protein of Formula (II) comprises SEQ ID NO: 20.

In another embodiment, two fusion proteins of Formula (III) above and two fusion proteins of B-(optional linker)-D-(optional linker)-E (Formula IV) can be assembled into a single construct, as depicted in FIG. 2 (2Dm2m). The fusion protein of Formula (III) can comprise SEQ ID NO: 19 and the fusion protein of Formula (IV) can comprise SEQ ID NO: 18.

The individual fusion proteins can be joined in the manner typical of IgG type constructs, such as by disulfide bridges between the constant heavy and constant light regions and between the Fc regions. Two or more fusion proteins joined as a single construct desirably can provide a multivalent (bivalent, tetravalent, or even octavalent) molecule.

Thus, constructs comprising two or more (e.g., two, three, four, five, six, seven, eight, nine, ten, or more) of the inventive fusion proteins also are encompassed by the invention.

In one embodiment, the fusion protein is assembled (e.g., self-assembled) to form one of the constructs depicted in FIG. 2, wherein A denotes an antibody or antibody fragment (e.g., m36.4 eAd), B denotes the inventive polypeptide (e.g., mD1.22), C denotes an immunoglobulin light chain constant region (e.g., human IgG1 kappa light chain constant region), D denotes an immunoglobulin heavy chain constant region (e.g., human IgG1 heavy chain constant region), and E denotes an Fc region (e.g., the Fc region from human IgG1).

The polypeptide and fusion protein can be PEGylated, or coupled to polymers of similar structure, function and purpose, to confer enhanced stability and half-life. PEGylation can provide increased half-life and resistance to degradation without a loss in activity (e.g., binding affinity) relative to non-PEGylated (e.g., antibody) polypeptides. Since PEGylation may not be advantageous with respect to some targets, in particular, those epitopes which are sterically-obstructed, the polypeptide or fusion protein should be minimally PEGylated so as not to negatively impact the accessibility to the size-restricted antigen. The polypeptide or fusion protein can be coupled to PEG or PEG-like polymers by any suitable means known in the art. Suitable PEG or PEG-like moieties can be synthetic or naturally occurring and include, but are not limited to, straight or branched chain polyalkylene, polyalkenylene or polyoxyalkylene polymers, or a branched or unbranched polysaccharide, such as a homo- or heteropolysaccharide. Preferred examples of synthetic polymers include straight or branched chain poly(ethylene glycol) (PEG), poly(propylene glycol), or poly(vinyl alcohol) and derivatives or substituted forms thereof. Substituted polymers for linkage to the domain antibodies also include substituted PEG, including methoxy(polyethylene glycol). Naturally occurring polymer moieties which can be used in addition to or in place of PEG include, for example, lactose, amylose, dextran, or glycogen, as well as derivatives thereof.

The polypeptide or fusion protein can be multimerized, as for example, hetero- or homodimers, hetero- or homotrimers, hetero- or homotetramers, or higher order hetero- or homomultimers. Multimerization can increase the strength of antigen binding, wherein the strength of binding is related to the sum of the binding affinities of the multiple binding sites. In particular, cysteine residue(s) can be introduced in the amino acid sequence of the polypeptide or fusion proteins, thereby allowing interchain disulfide bond formation in a multimerized form. The homodimeric or heterodimeric (or multimeric) fusion proteins can include combinations of the same or different fusion partners (e.g., eAds), such that more than one epitope can be targeted at a time by the same construct. Such epitopes can be proximally located in the target (e.g., on the HIV target) such that the binding of one epitope facilitates the binding of the multimeric fusion proteins to the second or more epitopes. The epitopes targeted by multimeric fusion proteins also can be distally situated.

Additional peptide sequences can be added to the fusion protein (or construct containing the fusion protein), which act to promote stability, purification, and/or detection. For example, a reporter peptide portion (e.g., green fluorescent protein (GFP), β-galactosidase, or a detectable domain thereof) can be used. Purification-facilitating peptide sequences include those derived or obtained from maltose binding protein (MBP), glutathione-S-transferase (GST), or thioredoxin (TRX). The polypeptide or fusion protein (or construct containing the fusion protein) also or alternatively can be tagged with an epitope which can be antibody purified (e.g., the Flag epitope, which is commercially available from Kodak (New Haven, Conn.)), a hexa-histidine peptide, such as the tag provided in a pQE vector available from QIAGEN, Inc. (Chatsworth, Calif.), or an HA tag (as described in, e.g., Wilson et al., *Cell*, 37, 767 (1984)).

The polypeptide and fusion protein (or construct containing the fusion protein) can be prepared by any suitable method. For example, the polypeptide and fusion protein can be prepared by synthesizing the amino acid sequence or by expressing a nucleic acid encoding the amino acid sequence in a cell and harvesting the resulting polypeptide or fusion protein from the cell. A combination of such methods also can be used. Methods of de novo synthesizing peptides and methods of recombinantly producing peptides are known in the art (see, e.g., Chan et al., *Fmoc Solid Phase Peptide Synthesis*, Oxford University Press, Oxford, United Kingdom, 2005; Peptide and Protein Drug Analysis, ed. Reid, R., Marcel Dekker, Inc., 2000; *Epitope Mapping*, ed. Westwood et al., Oxford University Press, Oxford, United Kingdom, 2000; Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, N Y, 1994).

Conjugates comprising the polypeptide or fusion protein (or construct containing the fusion protein) of the invention conjugated to cytotoxic agents, such as chemotherapeutic agents, toxin (e.g., an enzymatically active toxin of bacterial, fungal, plant or animal origin, or fragments thereof; a small molecule toxin), radioactive isotopes (i.e., a radioconjugate), or antiviral compounds (e.g., anti-HIV compounds) also are encompassed by the invention. Alternatively, the polypeptide or fusion protein (or construct containing the fusion protein) can be co-administered with the cytotoxic agents, antiviral compounds, and the like.

The conjugates comprising cytotoxic agents (e.g., toxins) can be used to target viral (e.g., HIV, such as HIV-1) infected cells and eradicate (destroy) such cells. For example, with a conjugate comprising (i) a cytotoxic agent and (ii) an antibody or antibody fragment containing construct as described herein, the (ii) antibody or antibody fragment portion of the conjugate targets (detects) surface proteins of viral infected cells and (i) the cytotoxic agent portion of the conjugate eradicates (destroys) the targeted viral infected cells. Preferably, the cells to be targeted are HIV (e.g., HIV-1) infected cells and the conjugate detects/targets the HIV (e.g., HIV-1) envelope glycoprotein expressed on the HIV infected cells. Administration of the conjugates can be used to destroy viral (e.g., HIV, such as HIV-1) infected cells in a subject, thereby leading to successful treatment (cure) of the viral (e.g., HIV) infection in the subject. Accordingly, the invention provides a method for treating a viral infection in a subject comprising administering the inventive conjugate to the subject, thereby treating (curing) the viral infection in the subject by destroying the viral-infected cells in the subject.

Methods for conjugating the polypeptide or fusion protein (or construct containing the fusion protein) to the cytotoxic agents, chemotherapeutic agents, toxins, antibacterial compounds, and antiviral compounds, and the like are well known in the art. For example, conjugates can be made using a variety of bifunctional protein coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Detectable agents, such as fluorescent compounds, also can be added to the polypeptide or fusion protein (or construct containing the fusion protein). Exemplary fluorescent detectable agents include fluorescein, fluorescein isothiocyanate, rhodamine, 5-dimethylamine-1-napthalenesulfonyl chloride, phycoerythrin and the like. The polypeptide or fusion protein also can be derivatized with detectable enzymes, such as alkaline phosphatase, horseradish peroxidase, glucose oxidase and the like. When the polypeptide or fusion protein construct is derivatized with a detectable enzyme, it is detected by adding additional reagents that the enzyme uses to produce a detectable reaction product. The polypeptide or fusion protein construct also can be derivatized with biotin, and detected through indirect measurement of avidin or streptavidin binding.

The invention also provides a nucleic acid encoding the amino acid sequence of the polypeptide or fusion protein. The nucleic acid can comprise DNA or RNA, and can be single or double stranded. Furthermore, the nucleic acid can comprise nucleotide analogues or derivatives (e.g., inosine or phophorothioate nucleotides and the like).

The nucleic acid can be provided as part of a construct comprising the nucleic acid and elements that enable delivery of the nucleic acid to a cell, and/or expression of the nucleic acid in a cell. Such elements include, for example, expression vectors, promoters, and transcription and/or translation sequences. Suitable vectors, promoters, transcription/translation sequences, and other elements, as well as methods of preparing such nucleic acids and constructs, are known in the art (e.g., Sambrook et al., supra; and Ausubel et al., supra).

The invention further provides a recombinant vector comprising the nucleic acid. Examples of suitable vectors include plasmids (e.g., DNA plasmids), yeast (e.g., *Saccharomyces*), and viral vectors, such as poxvirus, retrovirus, adenovirus, adeno-associated virus, herpes virus, polio virus, alphavirus, baculorvirus, and Sindbis virus. When the vector is a plasmid (e.g. DNA plasmid), the plasmid can be complexed with chitosan.

When the vector is for administration to a host (e g, human), the vector preferably has a low replicative efficiency in a target cell (e.g., no more than about 1 progeny per cell or, more preferably, no more than 0.1 progeny per cell are produced). Replication efficiency can readily be determined empirically by determining the virus titer after infection of the target cell.

The polypeptide, fusion protein, conjugate, or construct can be administered to a mammal in the form of a cell comprising a nucleic acid encoding the polypeptide or fusion protein, optionally in the form of a vector. Thus, the invention also provides a cell comprising a vector or nucleic acid encoding the polypeptide or fusion protein from which the polypeptide or fusion protein desirably is secreted. Any suitable cell can be used. Examples include host cells, such as *E. coli* (e.g., *E. coli* Tb-1, TG-2, DH5a, XL-Blue MRF' (Stratagene), SA2821, and Y1090), *Bacillus subtilis, Salmonella typhimurium, Serratia marcescens, Pseudomonas* (e.g., *P. aerugenosa*), *N. grassa*, insect cells (e.g., Sf9, Ea4), yeast (*S. cerevisiae*) cells, and cells derived from a mammal, including human cell lines. Specific examples of suitable eukaryotic cells include VERO, HeLa, 3T3, Chinese hamster ovary (CHO) cells, W138 BHK, COS-7, and MDCK cells. Alternatively and preferably, cells from a mammal, such as a human, to be treated in accordance with the methods described herein can be used as host cells. In one embodiment, the cell is a human B cell.

Methods of introducing vectors into isolated host cells and the culture and selection of transformed host cells in vitro are known in the art and include the use of calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, and electroporation (see, e.g., Sambrook et al., supra, Davis et al., *Basic Methods in Molecular Biology* (1986), and Neumann et al., *EMBO J.* 1, 841 (1982)). Desirably, the cell comprising the vector or nucleic acid expresses the nucleic acid encoding the polypeptide or fusion protein such that the nucleic acid sequence is transcribed and translated efficiently by the cell.

The polypeptide, fusion protein, conjugate, construct, nucleic acid, vector, or cell can be isolated. The term "isolated" as used herein encompasses compounds or compositions that have been removed from a biological environment (e.g., a cell, tissue, culture medium, body fluid, etc.) or otherwise increased in purity to any degree (e.g., isolated from a synthesis medium). Isolated compounds and compositions, thus, can be synthetic or naturally produced.

The polypeptide, fusion protein, conjugate, nucleic acid, vector, or cell can be administered to any host (e.g., mammal, preferably a human) in need thereof. As a result of administration of the polypeptide, fusion protein, conjugate, nucleic acid, vector, or cell to the mammal, viral infection (e.g., HIV infection) of the mammal is inhibited. The inventive method can prophylactically or therapeutically inhibit infection by any type of HIV, but preferably inhibits HIV-1 and/or HIV-2 infection. The inventive method can be used to inhibit infection by any HIV group (e.g., groups M and/or O), and subtype (e.g., clades A, B, C, D, E, EA, F, and/or G).

Additionally, the polypeptide, fusion protein, conjugate, nucleic acid, vector, or cell can be used to inhibit a broad range of viruses (see, e.g., *Principles of Virology: Molecular Biology, Pathogenesis, and Control*, Flint et al., eds., ASM Press: Washington, D.C. (2000), particularly Chapter 19). Examples of viruses that may be treated in accordance with the invention include, but are not limited to, Type C and Type D retroviruses, HTLV-1, HTLV-2, FIV, FLV, SIV, MLV, BLV, BIV, equine infectious virus, anemia virus, avian sarcoma viruses, such as Rous sarcoma virus (RSV), hepatitis type A, B, C, non-A and non-B viruses, arboviruses, varicella viruses, human herpes virus (e.g., HHV-6), measles, mumps, filovirus (e.g., Ebola, such as Ebola strains Sudan, Zaire, Cote d'Ivoire, and Reston), SARS, influenza, and rubella viruses.

When provided therapeutically, the polypeptide, fusion protein, conjugate, construct, nucleic acid, vector, cell, or composition thereof is provided at or after the diagnosis of viral (e.g., HIV) infection.

When provided prophylactically, the polypeptide, fusion protein, conjugate, construct, nucleic acid, vector, cell, or composition thereof is provided in advance of viral (e.g., HIV) infection, such as to patients or subjects who are at risk for being exposed to a virus (e.g., HIV) or who have been newly exposed to a virus (e.g., HIV). Examples of such patients and subjects include, for example, healthcare workers, fetuses, neonates, or infants (e.g., nursing infants) whose mothers are infected or at risk for being infected, intravenous drug users, recipients of blood transfusions, blood products, or transplantation tissue, and other individuals who have been exposed to a body fluid that contains or may contain HIV. The prophylactic administration of the polypeptide, fusion protein, conjugate, construct, nucleic acid, vector, cell, or composition thereof prevents, ameliorates, or delays viral (e.g., HIV) infection. In subjects who have been newly exposed to a virus (e.g., HIV) but who have not yet displayed the presence of the virus (as measured by PCR or other assays for detecting the virus) in blood or other body fluid, efficacious treatment with the polypeptide, fusion protein, conjugate, nucleic acid, vector, cell, or composition thereof partially or completely inhibits or delays the appearance of the virus or minimizes the level of the virus in the blood or other body fluid of the exposed individual.

The efficacy of the polypeptide, fusion protein, conjugate, construct, nucleic acid, vector, cell, or composition thereof can be assessed in various ways well known to the skilled practitioner. For instance, one of ordinary skill in the art will understand that a polypeptide or fusion protein of the invention is efficacious in treating or inhibiting a viral (e.g., HIV) infection in a subject by observing that the polypeptide or fusion protein reduces viral load or delays or prevents a further increase in viral load. Viral loads can be measured by methods that are known in the art, for example, using PCR assays to detect the presence of viral (e.g., HIV) nucleic acid or antibody assays to detect the presence of viral (e.g., HIV) protein in a sample (e.g., blood or another body fluid) from a subject or patient, or by measuring the level of circulating anti-viral (e.g., anti-HIV) antibodies in the patient. Efficacy of the polypeptide or fusion protein treatment also can be determined by measuring the number of CD4+ T cells in the HIV-infected subject. A treatment that delays or inhibits an initial or further decrease in CD4+ T cells in an HIV-positive subject or patient, or that results in an increase in the number of CD4+ T cells in the HIV-positive subject, can be considered efficacious.

The polypeptide, fusion protein, conjugate, construct, nucleic acid, vector, or cell can be formulated as a composition (e.g., pharmaceutical composition) comprising the polypeptide, fusion protein, conjugate, construct, nucleic acid, vector, or cell and a carrier (e.g., a pharmaceutically or physiologically acceptable carrier). Furthermore, the polypeptide, fusion protein, conjugate, construct, nucleic acid, vector, cell, or composition of the invention can be used in the methods described herein alone or as part of a pharmaceutical formulation.

Compositions (e.g., pharmaceutical compositions) comprising the polypeptide, fusion protein, conjugate, construct, nucleic acid, vector, or cell can include carriers, thickeners, diluents, buffers, preservatives, surface active agents and the like.

Suitable carriers and their formulations are described in A. R. Gennaro, ed., *Remington: The Science and Practice of Pharmacy* (19th ed.), Mack Publishing Company, Easton, Pa. (1995). Pharmaceutical carriers, include sterile water, saline, Ringer's solution, dextrose solution, and buffered solutions at physiological pH. Typically, an appropriate amount of a pharmaceutically acceptable salt is used in the formulation to render the formulation isotonic. The pH of the formulation is preferably from about 5 to about 8 (e.g., about 5.5, about 6, about 6.5, about 7, about 7.5, and ranges thereof). More preferably, the pH is about 7 to about 7.5. Further carriers include sustained-release preparations, such as semipermeable matrices of solid hydrophobic polymers containing the fusion protein, which matrices are in the form of shaped articles (e.g., films, liposomes, or microparticles). It will be apparent to those persons skilled in the art that certain carriers may be more preferable depending upon, for instance, the route of administration and concentration of composition being administered.

The composition (e.g., pharmaceutical composition) can comprise more than one polypeptide, fusion protein, conjugate, construct, nucleic acid, vector, or cell of the invention. Alternatively, or in addition, the composition can comprise one or more other pharmaceutically active agents or drugs. Examples of such other pharmaceutically active agents or drugs that may be suitable for use in the pharmaceutical composition include anticancer agents (e.g., chemotherapeutic drugs), antibiotics, antiviral drugs, antifungal drugs, cyclophosphamide, and combinations thereof. Suitable antiviral agents (e.g., anti-HIV agents) include, but are not limited to, nucleoside/nucleotide reverse transcriptase inhibitors (e.g., lamivudine, abacavir, zidovudine, stavudine, didanosine, emtricitabine, and tenofovir), non-nucleoside reverse transcriptase inhibitors (e.g., delavirdine, efavirenz, etravirine, and nevirapine), protease inhibitors (e.g., amprenavir, fosamprenavir, atazanavir, darunavir, indinavir, lopinavir, ritonavir, nelfinavir, saquinavir, and tipranavir), fusion or entry inhibitors (e.g., enfuvirtide and maraviroc), integrase inhibitors (e.g., raltegravir), and combination therapies thereof.

Suitable methods of administering a polypeptide, fusion protein, conjugate, construct, nucleic acid, vector, cell, or composition thereof to hosts are known in the art. The host can be any suitable host, such as a mammal (e.g., a rodent, such as a mouse, rat, hamster, or guinea pig, rabbit, cat, dog, pig, goat, cow, horse, primate, or human).

Administration can be topical (including ophthalmical, vaginal, rectal, intranasal, transdermal, and the like), oral, by inhalation, or parenteral (including by intravenous drip or subcutaneous, intracavity, intraperitoneal, or intramuscular injection). Topical intranasal administration refers to the delivery of the compositions into the nose and nasal passages through one or both of the nares and can comprise delivery by a spraying mechanism or droplet mechanism, or through aerosolization of the nucleic acid, vector, or fusion protein. Administration of the compositions by inhalant can be through the nose or mouth via delivery by a spraying or droplet mechanism. Delivery can also be directly to any area of the respiratory system (e.g., lungs) via intubation.

Formulations for topical administration include ointments, lotions, creams, gels, drops, suppositories, sprays, liquids, and powders. Conventional pharmaceutical carriers, aqueous, powder, or oily bases, thickeners, and the like may be necessary or desirable.

If the composition is to be administered parenterally, the administration is generally by injection. Injectables can be prepared in conventional forms, either as liquid solutions or suspensions, solid forms suitable for suspension in liquid prior to injection, or as emulsions. Additionally, parental administration can involve the preparation of a slow-release or sustained-release system, such that a constant dosage is maintained. Preparations for parenteral administration include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, anti-oxidants, chelating agents, and inert gases, and the like.

Compositions for oral administration include powders or granules, suspensions or solutions in water or non-aqueous media, capsules, sachets, or tablets. Thickeners, flavorings, diluents, emulsifiers, dispersing aids, or binders may be desirable.

Some of the compositions can potentially be administered as a pharmaceutically acceptable acid- or base-addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines.

The polypeptide, fusion protein, conjugate, construct, nucleic acid, vector, or cell can be administered with a pharmaceutically acceptable carrier and can be delivered to the mammal's cells in vivo and/or ex vivo by a variety of mechanisms well-known in the art (e.g., uptake of naked DNA, liposome fusion, intramuscular injection of DNA via a gene gun, endocytosis, and the like).

Additionally, probiotic therapies are envisioned by the present invention. Viable host cells containing the nucleic acid or vector of the invention and expressing the fusion protein or conjugate can be used directly as the delivery vehicle for the fusion protein to the desired site(s) in vivo. Preferred host cells for the delivery of the fusion protein or conjugate directly to desired site(s), such as, for example, to a selected body cavity, can comprise bacteria. More specifically, such host cells can comprise suitably engineered strain(s) of lactobacilli, enterococci, or other common bacteria, such as *E. coli*, normal strains of which are known to commonly populate body cavities. More specifically yet, such host cells can comprise one or more selected nonpathogenic strains of lactobacilli, such as those described by Andreu et al., *J. Infect. Dis.,* 171(5), 1237-43 (1995), especially those having high adherence properties to epithelial cells (e.g., vaginal epithelial cells) and suitably transformed using the nucleic acid or vector of the invention.

If ex vivo methods are employed, cells or tissues can be removed and maintained outside the body according to standard protocols known in the art. The compositions can be introduced into the cells via any gene transfer mechanism, such as calcium phosphate mediated gene delivery, electroporation, microinjection, or proteoliposomes. The transduced cells then can be infused (e.g., with a pharmaceutically acceptable carrier) or homotopically transplanted back into the mammal per standard methods for the cell or tissue type. Standard methods are known for transplantation or infusion of various cells into a mammal.

The exact amount of the composition required to treat a viral infection (e.g., HIV infection) will vary from mammal to mammal, depending on the species, age, gender, weight, and general condition of the mammal, the nature of the virus, the existence and extent of viral infection, the particular fusion proteins, nucleic acid, vector, or cell used, the route of administration, and whether other drugs are included in the regimen. Thus, it is not possible to specify an exact amount for every composition. However, an appropriate amount can be determined by one of ordinary skill in the art using only routine experimentation given the teachings herein. Effective dosages and schedules for administering the nucleic acid molecules, vectors, cells, and fusion proteins of the invention can be determined empirically, and making such determinations is within the skill in the art. The dosage ranges for the administration of the compositions are those large enough to produce the desired effect; however, the dosage should not be so large as to cause adverse side effects, such as unwanted cross-reactions, anaphylactic reactions, and the like. Dosage can vary, and can be administered in one or more (e.g., two or more, three or more, four or more, or five or more) doses daily, for one or more days. The composition can be administered before viral (e.g., HIV) infection or immediately upon determination of viral (e.g., HIV) infection and continuously administered until the virus is undetectable.

The polypeptide, fusion protein, conjugate, construct, nucleic acid, vector, cell, or composition thereof is administered to a host (e.g., mammal, such as a human) in an amount effective to prophylactically or therapeutically inhibit an HIV infection. The efficacy of the polypeptide, fusion protein, conjugate, construct, nucleic acid, vector, cell, or composition thereof as an HIV infection inhibitor may be determined by in vivo or in vitro parameters known in the art.

Any suitable dose of the polypeptide fusion protein, conjugate, nucleic acid, vector, cell, or composition thereof can be administered to a host. The appropriate dose will vary depending upon such factors as the host's age, weight, height, sex, general medical condition, previous medical history, and viral (e.g., HIV) infection progression and can be determined by a clinician. For example, the polypeptide, fusion protein, or conjugate can be administered in a dose of about 1 µg/kg to up to 100 mg/kg of body weight or more per day (e.g., 5 µg/kg, 10 µg/kg, 50 µg/kg, 100 µg/kg, 200 mg/kg, 300 µg/kg, 400 µg/kg, 500 µg/kg, 600 µg/kg, 700 µg/kg, 800 µg/kg, 900 mg/kg, 1 mg/kg, 2 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, and ranges thereof) to the host (e.g., mammal, such as a human). Several doses (e.g., 1, 2, 3, 4, 5, 6, or more) can be provided (e.g., over a period of weeks or months).

When the vector is a viral vector, a suitable dose can include about $1 \times 10^5$ to about $1 \times 10^{12}$ (e.g., $1 \times 10^6$, $1 \times 10^2$, $1 \times 10^8$, $1 \times 10^9$, $1 \times 10^{10}$, $1 \times 10^{11}$, and ranges thereof) plaque forming units (pfus), although a lower or higher dose can be administered to a host. For example, about $2 \times 10^8$ pfus can be administered (e.g., in a volume of about 0.5 mL).

The inventive cells can be administered to a host in a dose of between about $1 \times 10^5$ and $2 \times 10^{11}$ (e.g., $1 \times 10^6$, $1 \times 10^7$, $1 \times 10^8$, $1 \times 10^9$, $1 \times 10^{10}$, and ranges thereof) cells per infusion. The cells can be administered in, for example, one to three (e.g., two) infusions. In addition to the administration of the cells, the host can be administered a biological response modifier, such as interleukin 2 (IL-2).

The polypeptide or fusion protein (or construct containing the fusion protein) can be used in combination with other well-known viral (e.g., HIV) therapies and prophylactic vaccines already in use. The combination of the fusion protein of the invention can generate an additive or a synergistic effect with current treatments. The polypeptide or fusion protein (or construct containing the fusion protein) of the invention can be combined with other HIV and AIDS therapies and vaccines, such as highly active antiretroviral therapy (HAART), which comprises a combination of protease inhibitors and reverse transcriptase inhibitors, azidothymidine (AZT), structured treatment interruptions of HAART, cytokine immune enhancement therapy (e.g., interleukin (IL)-2, IL-12, CD40L+IL-12, IL-7, HIV protease inhibitors (e.g., ritonavir, indinavir, and nelfinavir, etc.), and interferons (IFNs)), cell replacement therapy, recombinant viral vector vaccines, DNA vaccines, inactivated virus preparations, immunosuppressive agents, such as Cyclosporin A, cyanovirin therapy (see, e.g., U.S. Pat. No. 6,015,876), scytovirin therapy (see, e.g., U.S. Pat. No. 7,491,798), and griffithsin therapy (see, e.g., U.S. Patent Application Publication 2009-0092557). Such therapies can be administered in the manner already in use for the known treatment providing a therapeutic or prophylactic effect (see, e.g., Silvestri et al. Immune Intervention in AIDS. In: *Immunology of Infectious Disease*, H. E. Kauffman, A. Sher, and R. Ahmed eds., ASM Press, Washington D.C. (2002)).

The following examples further illustrate the invention but, of course, should not be construed as in any way limiting its scope.

Example 1

This example describes the identification of single domain CD4 (D1) with improved soluble expression, stability, and specificity.

Structure-guided cavity filling and library screening were used to identify D1 mutants with improved soluble expression, stability and specificity. The screening yielded two mutants: mD1.22 (SEQ ID NO: 1) and mD1.23 (SEQ ID NO: 2) (see FIG. 1).

As depicted in Table 1, the mutants were significantly more soluble in *E. coli* periplasm and PBS than the previously identified D1 mutant (mD1.2; Chen et al., *J. Virol.*, 85: 9395-9405 (2011)).

TABLE 1

Properties of single domain CD4 mutants.

| Single Domain CD4 | Soluble Expression in *E. coli* (mg/L) | Solubility in PBS (pH 7.4) (mg/mL) |
|---|---|---|
| mD1.2 | 0.75 | >92.6 |
| mD1.22 | 5 | 175 |
| mD1.23 | 6 | ND |

ND = not determined

Example 2

This example demonstrates the characterization of mD1.22 and mD1.23.

The binding characteristics of mD1.2 (Chen et al., 2011, supra), mD1.22 (SEQ ID NO: 1), and mD1.23 (SEQ ID NO: 2) with HIV-1 gp140 were assessed at different D1 concentrations.

ELISAs were performed with $gp140_{Con-s}$, which is a consensus gp140 designed by aligning >1,000 sequences of group M (see Liao et al., *Virology*, 353: 268-282 (2006)), and $gp140_{CH12.0544.2}$. Bound mD1.2 and the mD1.22 and mD1.23 mutants were detected by HRP-conjugated anti-hexahistidine tag antibody (Sigma-Aldrich, St. Louis, Mo.).

Figure 3A:
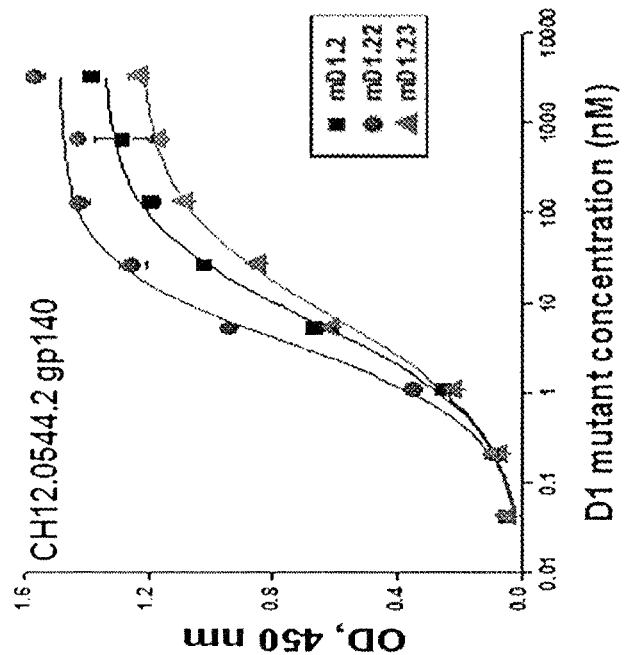
FIGS. 3A and 3B are graphs depicting the binding of the D1 mutants with two different HIV-1 envelope glycoproteins: gp140$_{Con-s}$ (A) and gp140$_{CH12.0544.2}$ (B). In each of the graphs, optical density at 450 nm is indicated on the y-axis and D1 mutant concentration (nM) is indicated on the x-axis.
Figure 3B:
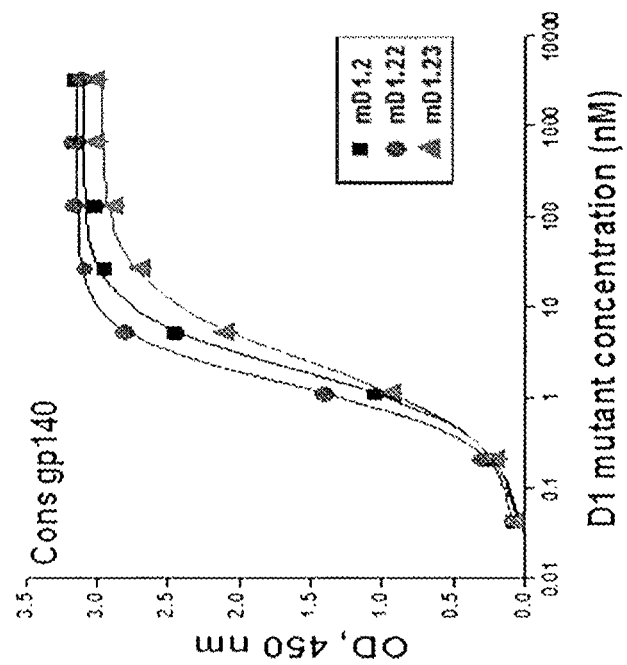

As shown in FIGS. 3A and 3B, both mutants were cross-reactive against the tested gp140s.

Binding of genetically diverse HIV-1 Envs also was analyzed by surface plama resonance (SPR) on a Biacore X100 appartus (GE Healthcare) using a single-cycle approach. Briefly, purified HIV-1 gp140 was diluted in sodium acetate (pH 5.0) and immobilized directly onto a CM5 sensor chip via the standard amine coupling method. The reference cell was injected with N-hydroxysuccinimide-1-ethyl-3-(3-dimethyaminopropy)carbodiimide and ethanolamine without injection of gp140. The D1 mutants and D1D2 were diluted with running buffer HSB-EP (100 mM HEPES (ph 7.4), 1.5 M NaCl, 30 mM EDTA, 0.5% surfactant 20). All analytes were tested at 500, 100, 20, 4, and 0.8 nM concentrations. Kinetic contants were calculated from the sensograms fitted with the monvalent binding model of the BiocoreX100 Evluation software 2.0.

In the SPR analysis with four HIV-1 Env gp140s, mD1.22 showed affinities comparable to, or higher than, those of mD1.2 (see Table 8).

Example 3

This example demonstrates that the D1 mutants maintain the functional activity of full-length CD4.

CD4 induces conformational changes in gp120 leading to exposure of CD4-inducible (CD4i) epitopes. To determine whether the D1 mutants induce such conformational changes, an CD4i antibody-based fusion protein, m36h1Fc (see Chen et al., *Proc. Natl. Acad. Sci. USA*, 105: 17121-17126 (2008)), was tested for binding to $gp140_{Con-s}$ in the absence or presence of mD1.2 (SEQ ID NO: 3), mD1.22 (SEQ ID NO: 1), or mD1.23 (SEQ ID NO: 2). The two-domain human CD4 (D1D2; SEQ ID NO: 5) was used a positive control and Fab b12, which is an HIV-1 broadly neutralizing antibody targeting the CD4-binding site on gp120 (see Roben et al., *J. Virol.*, 68: 4821-4828 (1994)), was used as the negative control.

Figure 4:
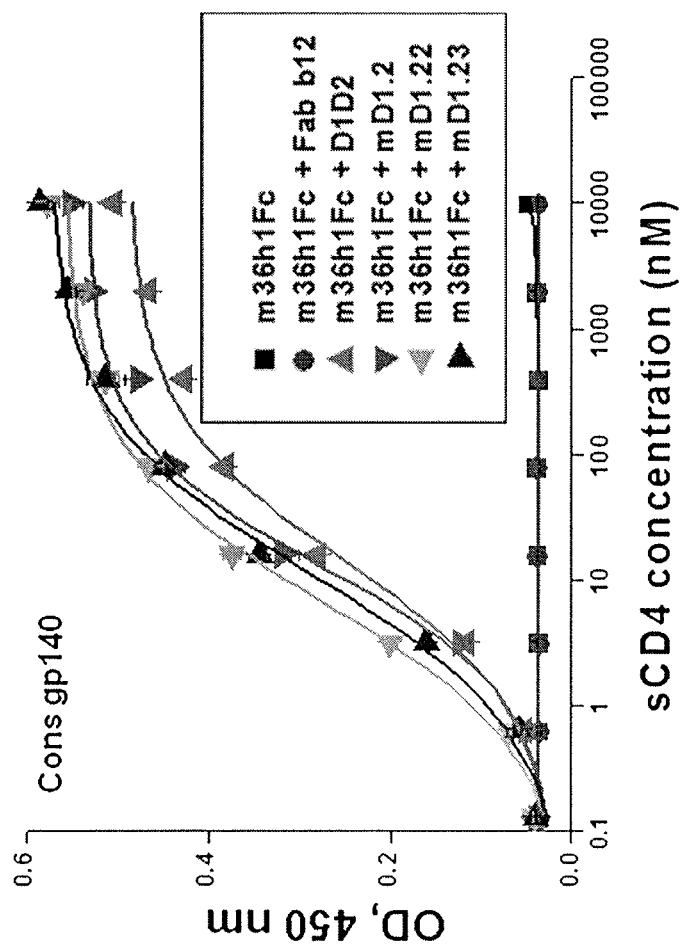
FIG. 4 is a graph depicting the enhancing effects of the D1 mutants on binding of CD4l antibody m36h1Fc to HIV-1 gp140$_{Con-s}$. Optical density at 450 nm is indicated on the y-axis and sCD4 concentration (nM) is indicated on the x-axis.

Binding of m36h1Fc to $gp140_{Con-s}$ was increased in the presence of the D1 mutants relative to the controls (see FIG. 4). Additionally, the binding m36h1Fc to $gp140_{Con-s}$ was increased or comparable to the binding observed in the presence of D1D2 and mD1.2, respectively (see FIG. 4).

Example 4

This example demonstrates the further characterization of the D1 mutants.

The secondary structure and thermal stability of mD1.2 (SEQ ID NO: 3), mD1.22 (SEQ ID NO: 1), and mD1.23 (SEQ ID NO: 2) were determined by circular dichroism (CD) spectroscopy. The purified proteins were dissolved in PBS at the final concentration of 0.33 mg/mL, and the CD spectra were recorded on AVIV Model 202 CD Spectrometer (Aviv Biomedical). Wavelength spectra were recorded at 25° C. using a 0.1-cm path-length cuvette for native structure measurements. Thermal stability was measured at 216 nm by recording the CD signal in the temperature range of 25-90° C. with heating rate 1° C./min. The temperature was recorded with an external probe sensor and the temperature inside the microcuvette was calculated by calibration; it was about 2-3° C. (range from 1.9 to 3.8° C. for temperatures from 20 to 80° C.) lower than the one measured by the external sensor. After heating, wavelength spectra were recorded at 90° C.

Figure 5:
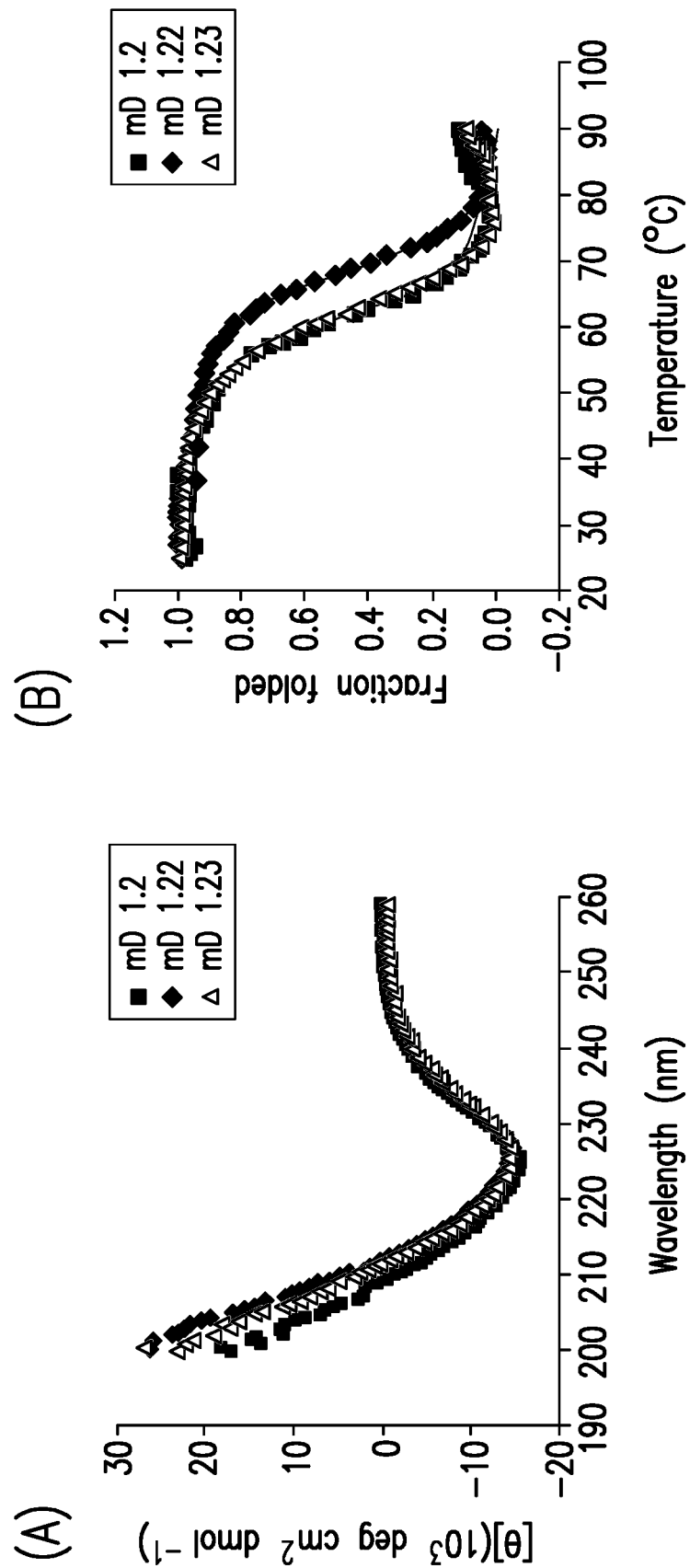
FIGS. 5A and 5B are graphs demonstrating that the D1 mutants consist primarily of β-strand secondary structures (A) and that mD1.22 has higher thermal stability than mD1.2 or mD1.23 (B).

As evidenced by FIG. 5A, mD1.22 and mD1.23 consist primarily of β-strand secondary structures. mD1.22 has higher thermal stability than mD1.2 and mD1.23 (see FIG. 5B).

Figure 6:
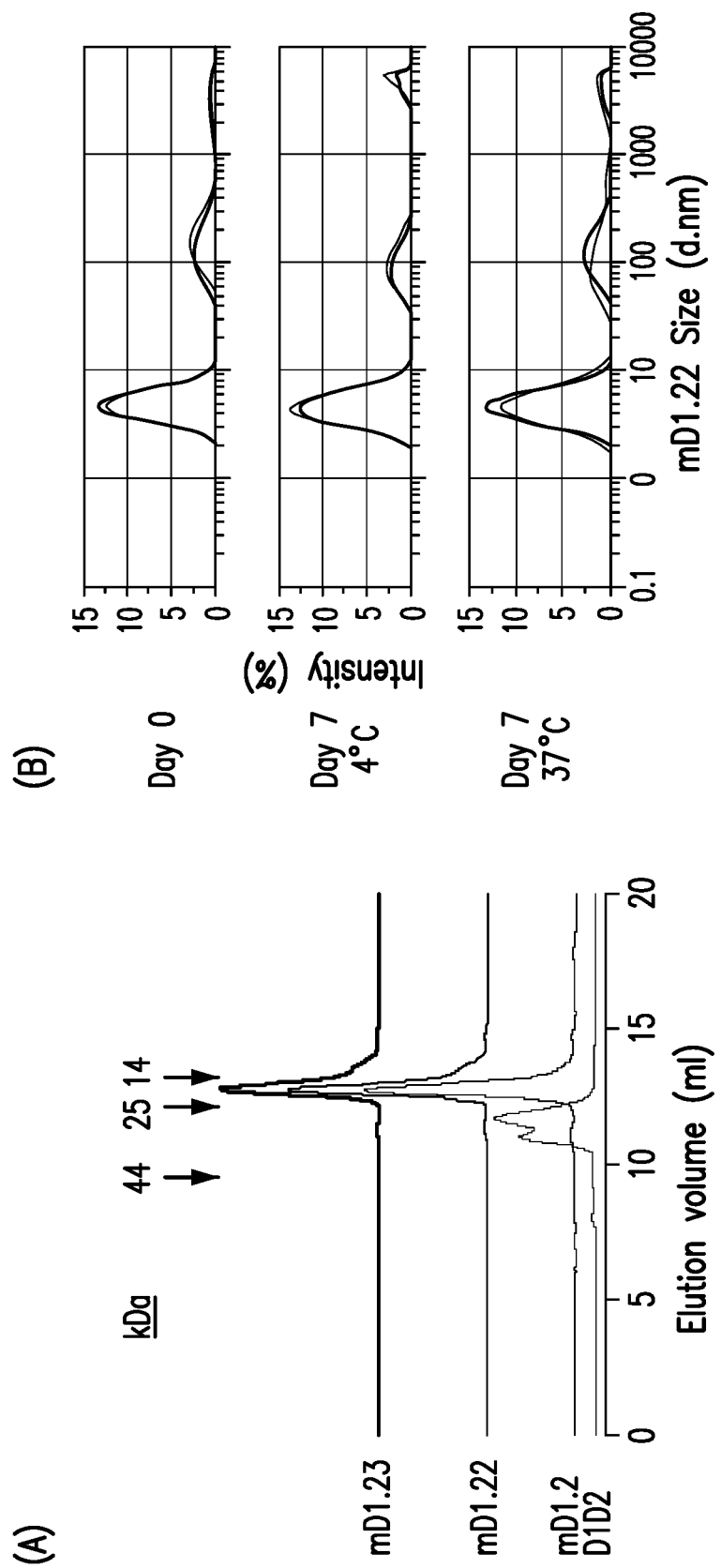
FIG. 6A is a graph demonstrating that the D1 mutants are monomeric (elute as one peak in size-exclusion chromatography).
FIG. 6B demonstrates that that mD1.22 does not tend to aggregate at high concentrations as shown by dynamic light scattering. Percent intensity at Day 0 or Day 7 at 4° C. or 37° C. is indicated on the y-axis and the size of mD1.22 (d.nm) is indicated on the x-axis.

Similar to mD1.2, mD1.22 and mD1.23 were uniformly monomeric in PBS at pH 7.4 as determined by size-exclusion chromatography. D1D2 also was monomeric but it was not eluted as a single peak (see FIG. 6A). mD1.22 did not tend to aggregate at high concentrations (10 mg/mL) as shown by dynamic light scattering (see FIG. 6B).

Example 5

This example demonstrates the characterization of Fc fusion proteins comprising the D1 mutants.

Fc-fusion proteins of D1D2, D1D2m (with A55V mutation; SEQ ID NO: 6), mD1.2, and mD1.22 (D1D2Fc, D1D2mFc, mD1.2Fc, and mD1.22Fc, respectively) were prepared using routine methods.

Figure 7:
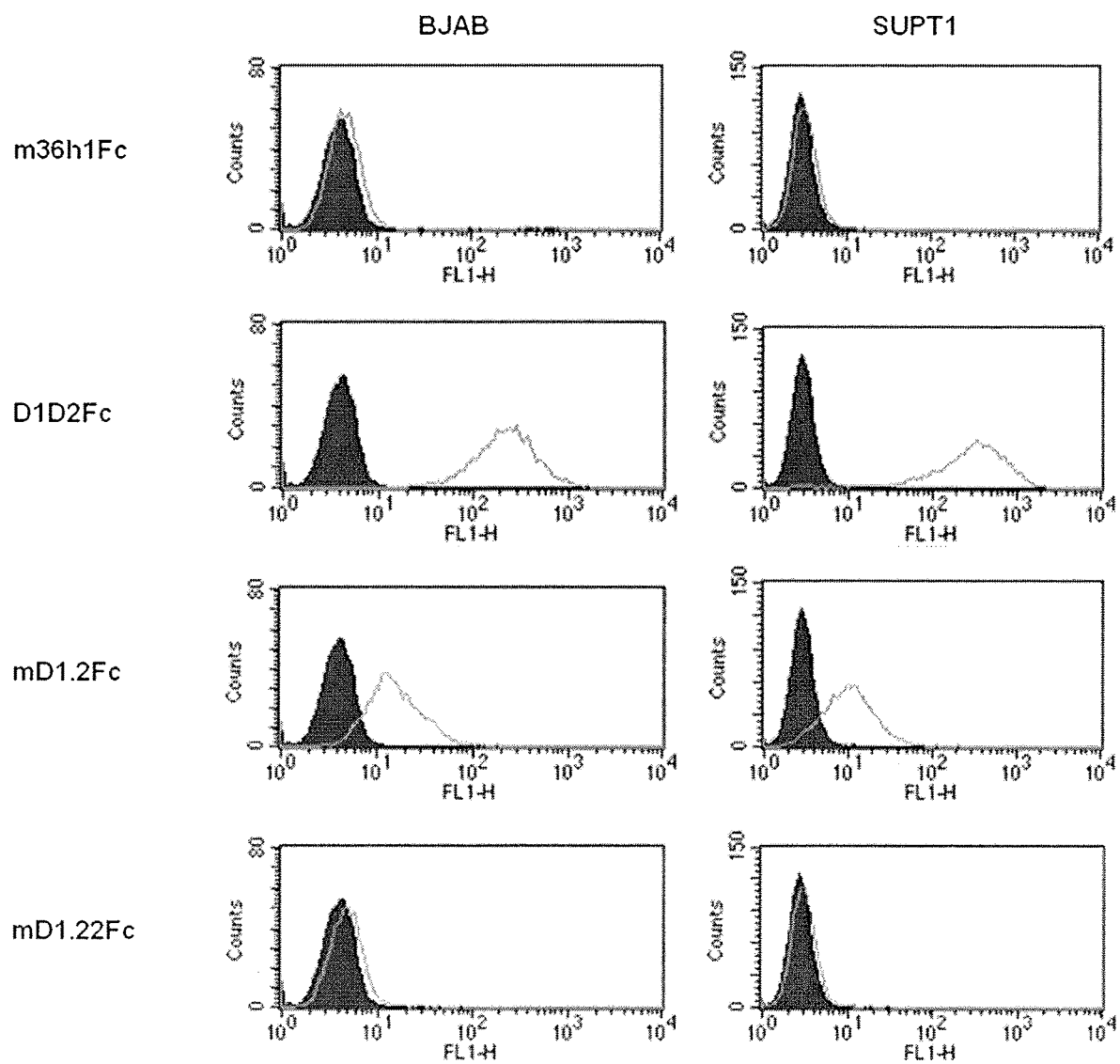
FIG. 7 demonstrates that an Fc-fusion protein of mD1.22 (mD1.22Fc) does not bind to MHC-expressing cells (human blood B (BJAB) and T (SUP-T1) cell lines). The dark curve contains reference cells only, while the light curve contains cells and Fc-fusion proteins.
Figure 8:
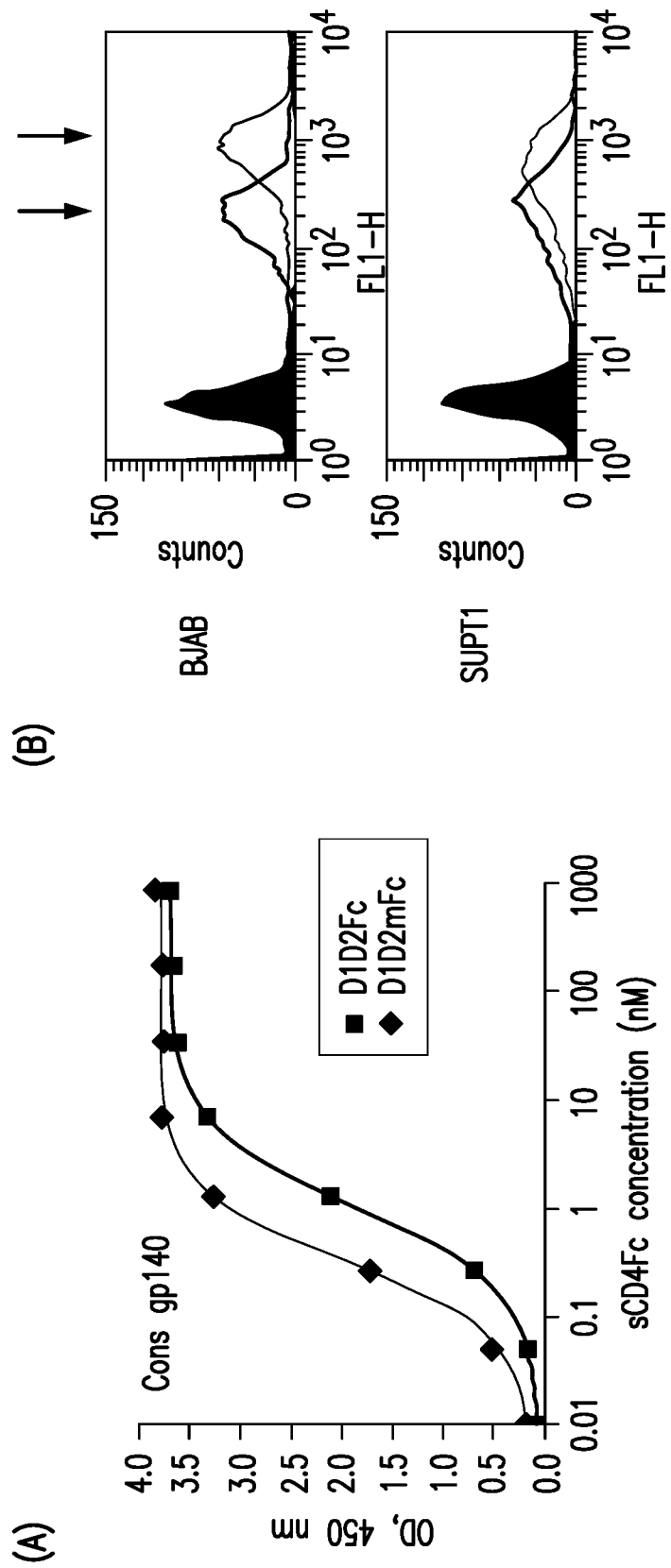
FIG. 8A is a graph demonstrating that the A55V mutant of D1D2Fc (D1D2mFc) shows increased binding to HIV-1 gp140$_{Con-s}$ as compared to D1D2Fc.
FIG. 8B demonstrates that the A55V mutant of D1D2Fc (D1D2mFc) has decreased interaction with human blood B and T cell lines (BJAB and SUP-T1) relative to D1D2Fc.

The binding of MHC-expression cells—human blood cell lines BJAB (B cell) and SUP-T1 (T cell)—was accessed for m36h1Fc (negative control), D1D2Fc, D1D2mFc, mD1.2Fc, and mD1.22Fc. As evidenced by FIGS. 7 and 8B, Fc fusions of mD1.22 or D1D2m show decreased binding with MHC-expression cells relative to the other fusion proteins.

Figure 9:
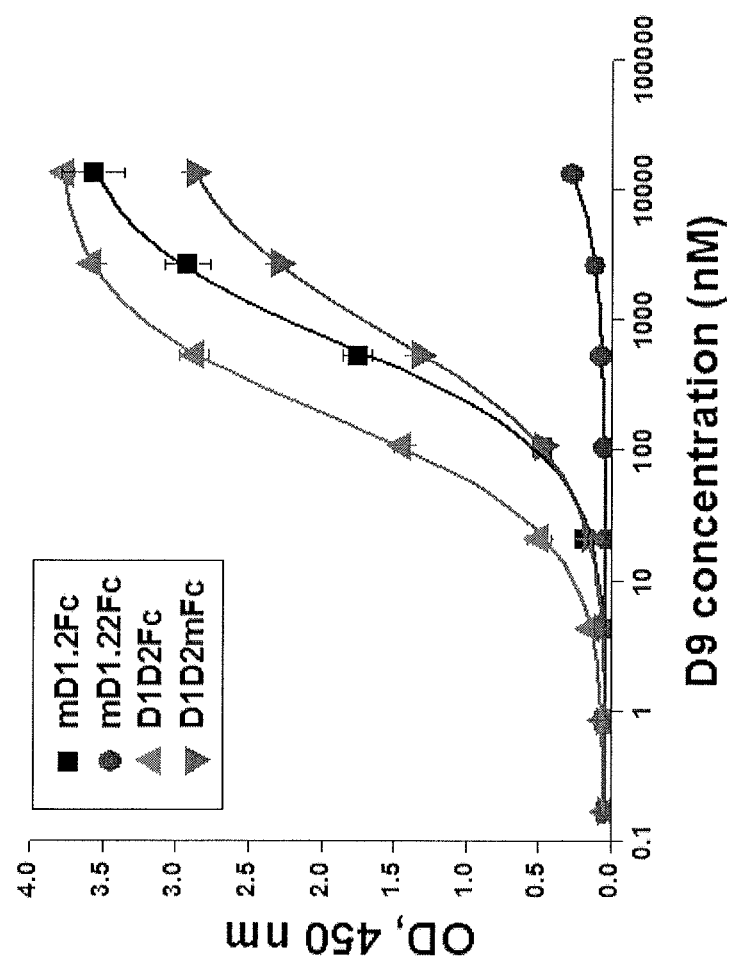
FIG. 9 is a graph demonstrating that the A55V mutation largely decreased binding of the CD4 D1-specific antibody D9 to mD1.22Fc and D1D2mFc, which suggests that the mutation induces conformational changes in D1. The optical density at 450 nm is indicated on the y-axis and the D9 concentration (nM) is indicated on the x-axis.

To determine if the A55V mutation results in conformational changes, interaction with a CD4 D1-specific antibody (D9) was assessed. As shown in FIG. 9, the presence of the A55V mutation in mD1.22Fc and D1D2mFc largely decreased binding with the D9 antibody. This suggests that the mutation induces conformation changes in D1. However, as noted above, the presence of the A55V mutation results in increased binding to H1V-1 gp140 (see FIG. 8A).

Example 6

This example demonstrates the characterization of bispecific multivalent fusion proteins comprising mD1.22.

Bispecific multivalent fusion proteins of mD1.22 (SEQ ID NO: 1) and m36.4 as exemplified in FIG. 2 (2Dm2m, 4Dm2m, and 6Dm2m) were prepared. m36.4 (SEQ ID NO: 15) is an engineered single human antibody domain targeting a CD4i epitope on HIV-1 gp120.

In each of the bispecific multivalent fusion proteins, A corresponds to m36.4, B corresponds to mD1.22, C corresponds to a light chain constant region, D corresponds to a heavy chain constant region, and E corresponds to an Fc region. In particular, 2Dm2m comprises two fusion proteins comprising SEQ ID NO: 18 and two fusion proteins comprising SEQ ID NO: 19. 4Dm2m comprises two fusion proteins comprising SEQ ID NO: 20 and two fusion proteins comprising SEQ ID NO: 21. 6Dm2m comprises two fusion proteins comprising SEQ ID NO: 22 and two fusion proteins comprising SEQ ID NO: 23.

Figure 10:
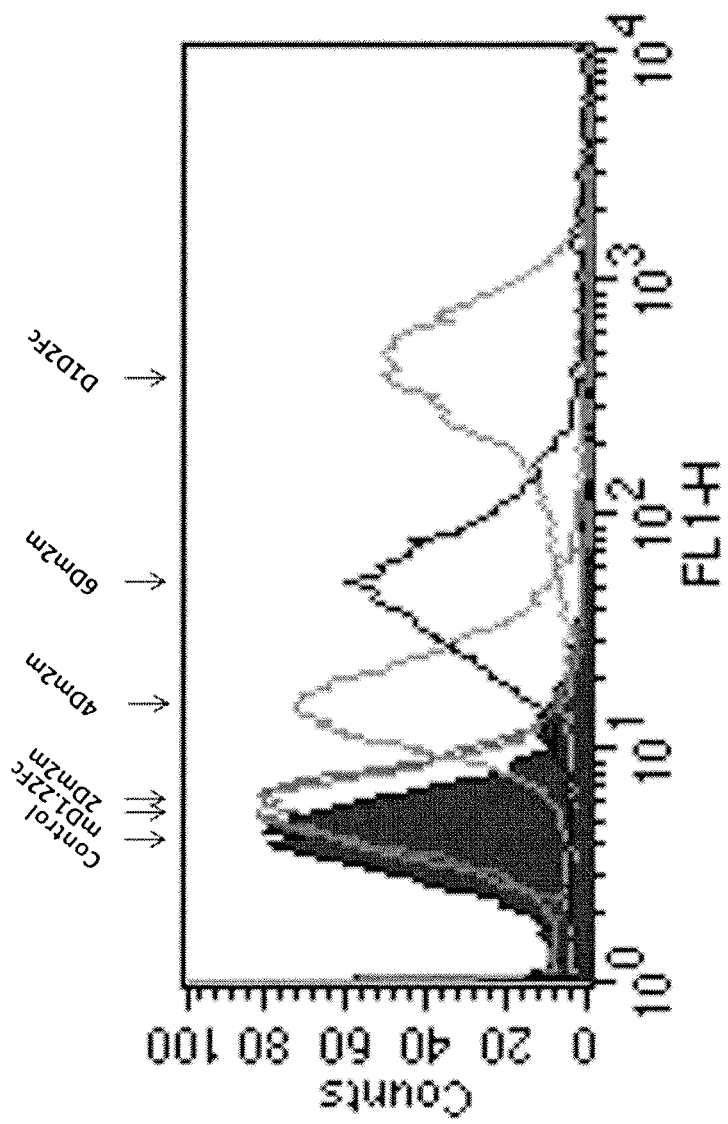
FIG. 10 is a graph demonstrating that mD1.22-36.4 fusion proteins (different valences) showed much lower binding to MHC-expressing cells (human blood B (BJAB) cell line) than D1D2Fc.

Similar to the results described in Example 5, the mD1.22-m36.4 multivalent fusion proteins showed much lower binding to MHC-expressing BJAB cells than D1D2Fc (see FIG. 10).

To determine the potency and breadth of HIV-1 neutralization by the D1 mutants, viruses pseudotyped with Envs from HIV-1 isolates representing clades A-E and using either CCR5 (R5) or CXCR4 (X4) or both (R5X4) as a coreceptor were included. Pseudoviruses were derived from 293T cells and a neutralization assay was performed in duplicate using HOS-CD4-CCR5 (for all R5 and dual tropic viruses) or HOS-CD4-CXCR4 cell lines as described in Chen et al., *Proc. Natl. Acad. Sci. USA*, 105: 17121-17126 (2008)). Luminescence was measured 48 hours post-infection and the percentage neutralization was calculated by the following formula: (1−average RLU of inhibitor-containing wells/average RLU or virus-only wells)×100. $I_{50}$ and $IC_{90}$ of neutralization were assigned for the inhibitor concentration at which 50% and 90% neutralization were observed, respectively.

As shown in Tables 2 and 3, mD1.22 and mD1.22-containing fusion proteins neutralized HIV-1 primary isolates from several different clades. Significantly, 4Dm2m and 6Dm2m were more potent than broadly neutralizing monoclonal antibody VRC01 (see Table 3).

Additionally, mD1.22 and mD1.22-containing fusion proteins inhibited HIV-1 envelope glycoprotein-mediated cell fusion (see Tables 4 and 5). As shown in Table 5, 4Dm2m and 6Dm2m are more potent than VRC01 in inhibiting HIV-1 envelope glycoprotein mediated cell-cell fusion.

In a TZM-bl cell-based assay (see Brown et al., *Virology*, 375: 529-538 (2008)) where TZM-bl cells and HIV-1 isolates randomly selected from each Glade from A to D, AE, and AG (total n=12) were used, 4Dm2m and 6Dm2m were much more potent than b12 and CD4-Ig and about 10-fold more potent than VRC01 when the geometric means of their $IC_{50}$s and $IC_{90}$s were compared (see Table 6).

In another TZM-bl cell-based assay using a panel of pseudoviruses with Envs derived from 41 HIV-1 isolates predominantly circulating in China (see Yao et al., *J. Biol. Chem.*, 287: 6788-6796 (2012); and Shang et al., *J. Biol. Chem.*, 286: 14531-14541 (2011)), 4Dm2m and 6Dm2m were compared to T20 (enfuvirtide), which is an FDA-approved peptide inhibitor derived from the HIV-1 Env gp41 C-terminal heptad repeat (CHR), C34, which is another potent CHR peptide inhibitor, and CD4-Ig for neutralizing activities against the panel (see Table 7). 4Dm2m and 6Dm2m neutralized all viruses with $IC_{50}$ geometric mean values of approximately 0.20 nM, which are about 50-fold (P=0.002, Student's paired t test), 16-fold (P<0.001, Student's parent t test), and 200-fold (P<0.001, Student's paired t test) lower than those (11, 3.5, and 42 nM) of T20, C34, and CD4-Ig respectively (see Table 7). The superior potencies of 4Dm2m and 6Dm2m also were observed when the $IC_{90}$s were compared.

Figure 11:
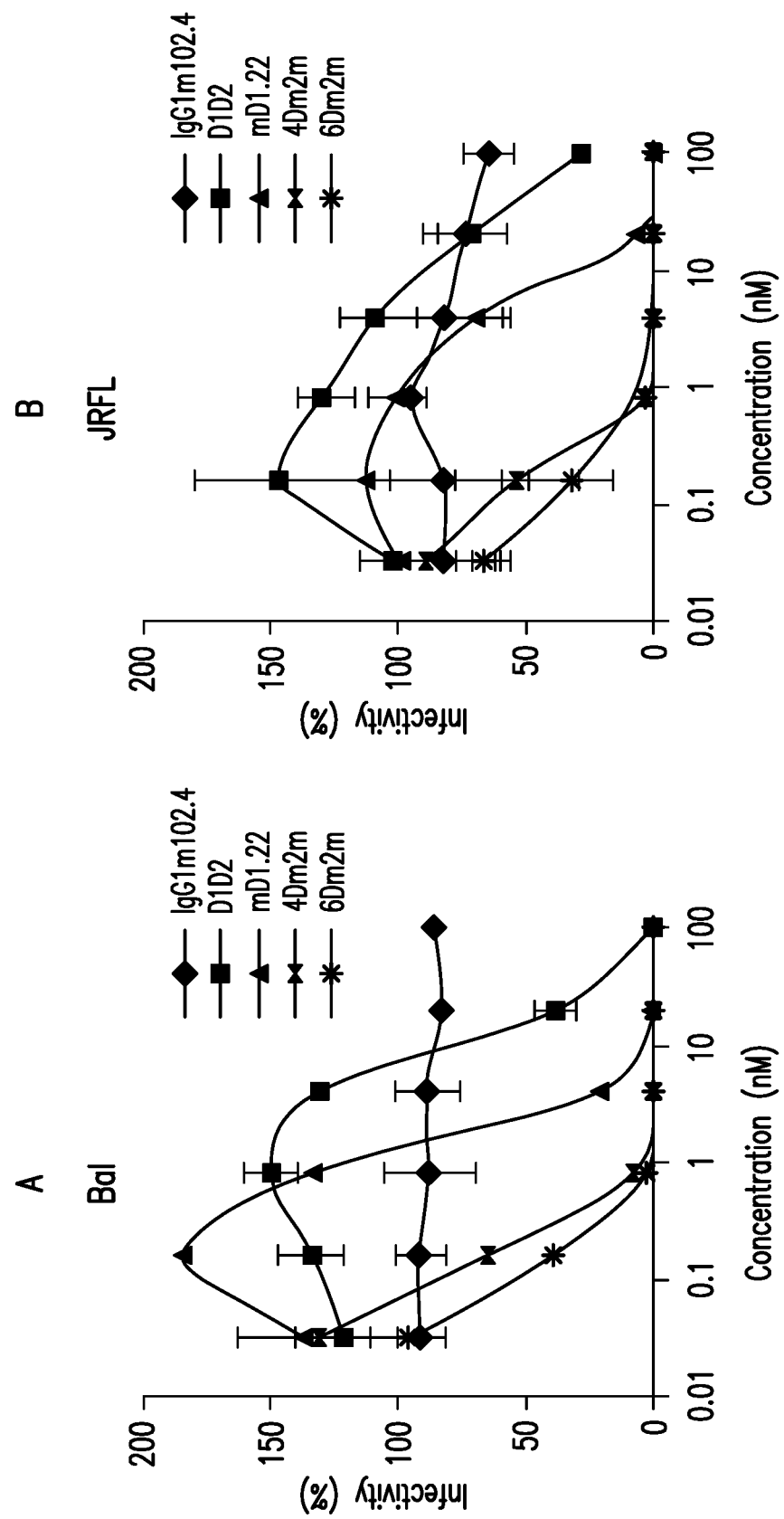
FIGS. 11A and 11B are graphs depicting that 4Dm2m and 6Dm2m do not enhance HIV-1 infectivity to two HIV-1 primary isolates (Ba1 in FIG. 11A and JRFL in FIG. 11B) at low concentrations in contrast to D1D2. In each graph, percent infectivity is indicated on the y-axis and concentration (nM) is indicated on the x-axis. IgG1 m102.4 (see Zhu et al., *J. Infect. Dis.*, 197: 846-853 (2008)), is a control antibody specific to Nipah and Hendra viruses that did not inhibit any of the viruses.

4Dm2m and 6Dm2m also have been shown to not enhance HIV-1 infectivity at low concentrations, which is in contrast to D1D2 (see FIG. 11).

Example 7

This example demonstrates the solubility, stability, and aggregration propensity of the bispecific multivalent fusion proteins.

To evaluate the potential for further development as drugs, several drug-related properties, including solubility, stability, and aggregation propensity were tested. 4Dm2m and 6Dm2m in PBS were concentrated to 25.0 and 25.9 mg/ml, respectively, without visible precipitation after high-speed centrifugation. They were stored at 4° C. for 2 weeks, and no additional precipitation was observed, suggesting high solubility of the proteins.

To test whether soluble aggregates of 4Dm2m and 6Dm2m formed during prolonged incubation, dynamic light scattering (DLS) was used. Proteins concentrated to 10 mg/ml in PBS were stored at 80° C. and slowly thawed on ice before measurements. The results showed that the particles of 4Dm2m and m909, a control human antibody in the IgG1 format (see Feng et al., *Arthritis Res. Ther.* 13: R59 (2011)), were predominantly small (average diameters, 16.3 and 12.7 nm, respectively). The minor aggregates of 4Dm2m disappeared within the first day of incubation at both 4° C. and 37° C., while m909 aggregation continued to occur following the incubation at 37° C. In comparison, about 30 to 50% of the CD4-Ig particles were large, with average diameters of approximately 100 nm, and the aggregation persisted during the whole period of incubation. 6Dm2m partially aggregated after the freeze-thaw cycle; although the aggregation was weakened following the incubation, it led to a relatively wide particle size distribution.

These results suggest that like typical IgG1s, 4Dm2m has a low aggregation propensity, which is lower than that of CD4-Ig.

Figure 12A:
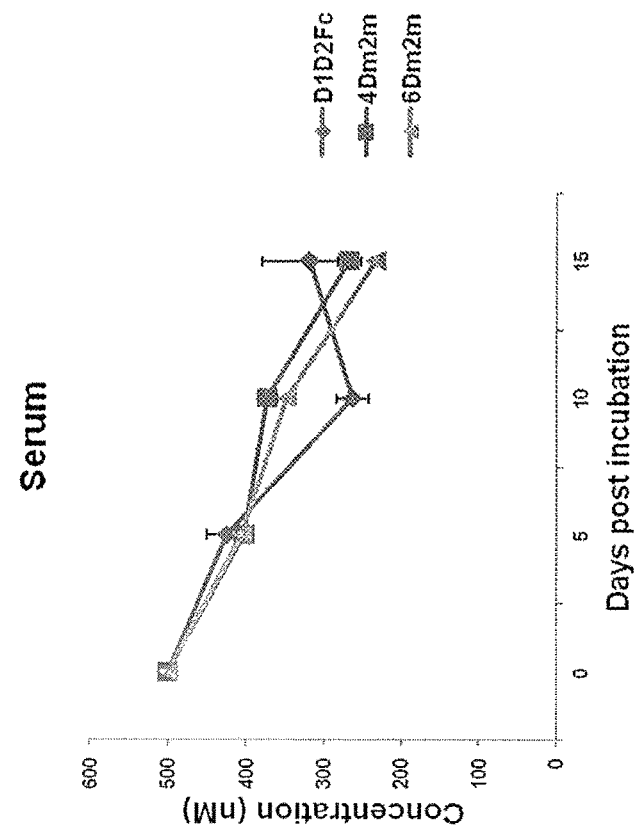
FIGS. 12A and 12B are graphs demonstrating the stability of 4Dm2m and 6Dm2m against degration in PBS and in human serum. In each graph, concentration (nM) is indicated on the y-axis and incubation time (days) is indicated on the x-axis. CD4-Ig is used as a control.

The proteins were then assessed for their stability against degradation during 15 days of incubation with PBS (see FIG. 12A) or human serum (see FIG. 12B) at 37° C. Incubation in PBS for 10 days caused no significant decrease in the amount of functional 4Dm2m, whereas about 20% and 30%, respectively, of 6Dm2m and CD4-Ig lost binding activity to gp140$_{Con-s}$ (see FIG. 12A). 4Dm2m began to be degraded and 6Dm2m continued to be degraded thereafter, while CD4-Ig appeared to be stable. Finally, about 90% of 4Dm2m remained functional, slightly more than those (80%) of 6Dm2m and CD4-Ig.

Figure 12B:
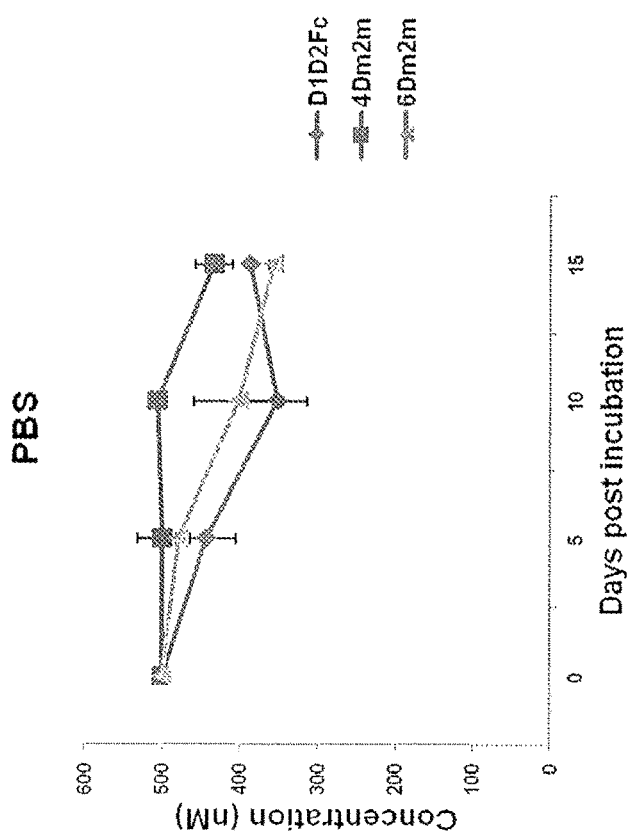

With human serum, levels of all proteins declined at similar rates during the first 5 days of incubation (see FIG. 12B). However, degradation of 4Dm2m and 6Dm2m became slower than that of CD4-Ig during the next 5 days of incubation. At the end of the measurement period, the level of CD4-Ig that retained binding activity was slightly higher than that for functional 4Dm2m and 6Dm2m, but the differences in the amounts were not statistically significant.

TABLE 2

Neutralization of pseudotyped HIV-1 by mD1.22 of different valences.

| | | | m36.4 | | mD1.22 | | mD1.22Fc | | 2Dm2m | |
|---|---|---|---|---|---|---|---|---|---|---|
| Virus | Clade | Tropism | $IC_{50}{}^a$ | $IC_{90}{}^b$ | $IC_{50}$ | $IC_{90}$ | $IC_{50}$ | $IC_{90}$ | $IC_{50}$ | $IC_{90}$ |
| Bal | B | R5 | 16 ± 1 | 75 ± 18 | 2.1 ± 0.1 | 5.2 ± 0.2 | 0.40 ± 0.00 | 1.9 ± 0.2 | 0.34 ± 0.15 | 0.59 ± 0.05 |
| JRFL | B | R5 | 18 ± 5 | 106 ± 4 | 2.9 ± 0.4 | 25 ± 1 | 1.2 ± 0.1 | 25 ± 6 | 0.090 ± 0.008 | 0.59 ± 0.06 |

| | 4Dm2m | | 6Dm2m | |
|---|---|---|---|---|
| Virus | $IC_{50}$ | $IC_{90}$ | $IC_{50}$ | $IC_{90}$ |
| Bal | 0.12 ± 0.01 | 0.36 ± 0.06 | 0.063 ± 0.004 | 0.22 ± 0.02 |
| JRFL | 0.060 ± 0.014 | 0.29 ± 0.09 | 0.043 ± 0.004 | 0.21 ± 0.01 |

[a]Antibody concentration (nM) resulting in 50% inhibition of virus infection.
[b]Antibody concentration (nM) resulting in 90% inhibition of virus infection.

TABLE 3

Neutralization of HIV-1 pseudotyped with Envs from different clades by 4Dm2m, 6Dm2m, and bnmAbs.

| | | | 2G12 | | VRC01 | | 4Dm2m | | 6Dm2m | |
|---|---|---|---|---|---|---|---|---|---|---|
| Virus | Clade | Tropism | $IC_{50}{}^a$ | $IC_{90}{}^b$ | $IC_{50}$ | $IC_{90}$ | $IC_{50}$ | $IC_{90}$ | $IC_{50}$ | $IC_{90}$ |
| 92UG037.8 | A | R5 | 0.53 ± 0.10 | 63 ± 4 | 0.33 ± 0.11 | 3.8 ± 4.3 | 0.051 ± 0.001 | 0.45 ± 0.01 | 0.14 ± 0.08 | 2.1 ± 0.6 |
| Bal | B | R5 | 3.1 ± 0.0 | 41 ± 1 | 0.11 ± 0.04 | 0.56 ± 0.01 | 0.15 ± 0.04 | 0.50 ± 0.07 | 0.12 ± 0.01 | 0.38 ± 0.02 |
| JRFL | B | R5 | 3.0 ± 0.5 | 13 ± 3 | 0.31 ± 0.21 | 0.82 ± 0.40 | 0.14 ± 0.01 | 0.39 ± 0.04 | 0.10 ± 0.01 | 0.43 ± 0.04 |
| JRCSF | B | R5 | 0.58 ± 0.17 | 9.3 ± 8.0 | 0.28 ± 0.18 | 5.6 ± 2.1 | 0.29 ± 0.18 | 3.0 ± 2.9 | 0.21 ± 0.14 | 1.0 ± 0.1 |
| AD8 | B | R5 | 1.2 ± 0.1 | 18 ± 3 | 0.36 ± 0.13 | 4.3 ± 0.4 | 0.13 ± 0.01 | 0.74 ± 0.06 | 0.11 ± 0.01 | 0.60 ± 0.08 |
| R2 | B | R5 | 0.68 ± 0.11 | 4.6 ± 0.1 | 0.34 ± 0.01 | 4.4 ± 0.1 | 0.028 ± 0.011 | 0.43 ± 0.18 | <0.021 | 0.14 ± 0.04 |
| IIIB | B | X4 | 1.5 ± 0.0 | 9.3 ± 2.4 | 0.26 ± 0.01 | 0.83 ± 0.04 | 0.037 ± 0.001 | 0.10 ± 0.01 | <0.021 | 0.086 ± 0.006 |
| NL4-3 | B | X4 | 1.3 ± 0.2 | 18 ± 10 | 0.25 ± 0.02 | 2.6 ± 0.6 | 0.094 ± 0.002 | 0.15 ± 0.02 | 0.068 ± 0.004 | 0.19 ± 0.02 |
| 89.6 | B | R5X4 | 1.3 ± 1.1 | 43 ± 11 | 0.37 ± 0.10 | 14 ± 2 | <0.021 | <0.021 | <0.021 | <0.021 |
| GXC | C | R5 | —[c] | — | 2.1 ± 0.1 | 6.6 ± 4.8 | 0.61 ± 0.36 | 4.0 ± 0.0 | 0.63 ± 0.06 | 1.7 ± 0.1 |
| Z2Z6 | D | R5 | 0.70 ± 0.01 | 14 ± 2 | 0.11 ± 0.01 | 0.85 ± 0.14 | 0.14 ± 0.04 | 1.1 ± 0.1 | 0.045 ± 0.006 | 0.50 ± 0.00 |
| CM243 | E | R5 | — | — | 0.53 ± 0.11 | 9.5 ± 2.1 | 0.29 ± 0.11 | 1.2 ± 0.6 | 0.15 ± 0.05 | 1.8 ± 0.4 |
| GXE | E | R5 | — | — | 2.0 ± 0.4 | 26 ± 23 | 0.83 ± 0.11 | 8.2 ± 1.3 | 0.83 ± 0.38 | 6.3 ± 5.2 |
| Arithmetic means[d] | | | 1.4 | 23 | 0.57 | 6.1 | 0.22 | 1.6 | 0.19 | 1.2 |
| Geometric means[d] | | | 1.2 | 17 | 0.37 | 3.4 | 0.12 | 0.56 | 0.083 | 0.46 |

[a]Antibody concentration (nM) resulting in 50% inhibition of virus infection.
[b]Antibody concentration (nM) resulting in 90% inhibition of virus infection.
[c]No significant neutralization at the highest antibody concentration (67 nM) tested.
[d]Arithmetic and geometric means were calculated for all viruses including those with values <0.021 nM, which were assigned a value of 0.01. The means for 2G12 were calculated based on the values with 10 isolates that were significantly neutralized.

TABLE 4

Inhibition of HIV-1 Env-mediated cell-cell fusion by mD1.22 of different valences.

| | | | m36.4 | | mD1.22 | | mD1.22Fc | |
|---|---|---|---|---|---|---|---|---|
| Virus | Clade | Tropism | $IC_{50}{}^a$ | $IC_{90}{}^b$ | $IC_{50}$ | $IC_{90}$ | $IC_{50}$ | $IC_{90}$ |
| Bal | B | R5 | 11 ± 1 | 235 ± 49 | 21 ± 0 | 108 ± 4 | 24 ± 4 | 135 ± 21 |
| JRFL | B | R5 | 128 ± 5 | 1075 ± 35 | 66 ± 1 | 208 ± 4 | 66 ± 1 | >222 |

| | 2Dm2m | | 4Dm2m | | 6Dm2m | |
|---|---|---|---|---|---|---|
| Virus | $IC_{50}$ | $IC_{90}$ | $IC_{50}$ | $IC_{90}$ | $IC_{50}$ | $IC_{90}$ |
| Bal | 21 ± 6 | 113 ± 39 | 4.1 ± 0.1 | 13 ± 3 | 3.0 ± 0.0 | 5.0 ± 0.8 |
| JRFL | 7.5 ± 0.0 | 80 ± 9 | 1.6 ± 0.7 | 11 ± 2 | 0.46 ± 0.07 | 10 ± 3 |

[a]Antibody concentration (nM) resulting in 50% inhibition of cell-cell fusion.
[b]Antibody concentration (nM) resulting in 90% inhibition of cell-cell fusion.

TABLE 5

Inhibition of HIV-1 Env-mediated cell-cell fusion by 4Dm2m, 6Dm2m, and bnmAbs.

| | | | 2G12 | | VRC01 | | 4Dm2m | | 6Dm2m | |
|---|---|---|---|---|---|---|---|---|---|---|
| Virus | Clade | Tropism | IC$_{50}$[a] | IC$_{90}$[b] | IC$_{50}$ | IC$_{90}$ | IC$_{50}$ | IC$_{90}$ | IC$_{50}$ | IC$_{90}$ |
| Bal | B | R5 | 38 ± 31 | >67 | 2.6 ± 0.0 | 24 ± 2 | 4.1 ± 0.1 | 12 ± 0 | 2.3 ± 0.2 | 6.7 ± 2.2 |
| JRFL | B | R5 | 14 ± 2 | 67 ± 5 | 3.1 ± 0.6 | 21 ± 1 | 3.6 ± 0.2 | 8.8 ± 0.4 | 2.3 ± 0.3 | 5.8 ± 1.1 |

[a]Antibody concentration (nM) resulting in 50% inhibition of cell-cell fusion.
[b]Antibody concentration (nM) resulting in 90% inhibition of cell-cell fusion.

TABLE 6

Neutralization of HIV-1 in TZM-bl cell-based assays

| | | | IC$_{50}$ (nM)[a] | | | | | IC$_{90}$ (nM)[a] | | | | |
|---|---|---|---|---|---|---|---|---|---|---|---|---|
| Virus | Clade | Tropism | b12[a] | VRC01[b] | D1D2Fc | 4Dm2m | 6Dm2m | b12 | VRC01 | D1D2Fc | 4Dm2m | 6Dm2m |
| KNH1088.EC5 | A | R5 | 117 | 3.0 | >250 | 0.48 | 1.0 | >167 | 18 | >250 | 18 | 33 |
| KNH1144.EC1 | A | R5 | >167 | 2.2 | 4.8 | 0.081 | 0.11 | >167 | 9.5 | 42 | 1.0 | 1.1 |
| Bal.EC1 TC | B | R5 | 1.2 | 0.39 | 0.60 | 0.057 | 0.045 | 3.6 | 5.2 | 3.2 | 0.22 | 0.20 |
| BZ167.ec9 | B | X4 | 14 | 6.4 | 13 | 0.077 | 0.10 | >167 | 31 | 60 | 0.50 | 0.76 |
| GS-015.EC12 | C | R5 | 0.085 | >167 | 0.20 | 0.022 | 0.027 | 1.6 | >167 | 3.2 | 0.17 | 0.17 |
| PBL286.VRC36aPV | C | R5 | 4.0 | 2.1 | 87 | 2.0 | 2.1 | 19 | 10 | >250 | 14 | 12 |
| A07412VRC12A | D | R5 | 12 | 1.3 | 57 | 0.75 | 0.76 | >167 | 6.0 | >250 | 5.7 | 6.1 |
| 57128.VRC18 | D | R5 | 2.3 | >167 | 5.4 | 0.40 | 0.44 | 30 | >167 | 41 | 2.8 | 2.6 |
| CM240.EC1 | AE | R5 | 82 | 0.66 | 20 | 0.45 | 0.40 | >167 | 11 | >250 | 3.7 | 3.6 |
| N1 1046.e3 PV | AE | R5 | 138 | 4.2 | 183 | 3.5 | 3.1 | >167 | 18 | >250 | 27 | 30 |
| CAM0015BBY.EC3 | AG | R5 | 81 | 21 | 41 | 0.72 | 1.4 | >167 | >167 | >250 | 7.4 | 7.6 |
| 55815.EC3 | AG | R5 | >167 | 0.33 | 6.2 | 0.084 | 0.077 | >167 | 2.6 | 116 | 0.61 | 0.67 |
| Arithmetic mean[c] | | | 71 | 37 | 60 | 0.72 | 0.80 | 138 | 59 | 172 | 6.8 | 8.2 |
| Geometric mean[c] | | | 17 | 4.2 | 14 | 0.28 | 0.32 | 67 | 21 | 82 | 2.4 | 2.6 |

[a]The assay was performed in duplicate. Results are presented as mean without standard deviation. Means are calculated only when the difference between results for the duplicate assays was within 3-fold.
[b]The bnAbs b12 and VRC01 used in the neutralization assay are in IgG1 format.
[c]Arithmetic and geometric means were calculated for all viruses including those with values >167 nM, which were assigned a value of 200, and those with values >250, which were assigned a value of 300.

TABLE 7

Neutralization of HIV-1 isolates predominantly circulating in China in TZM-bl cell-based assays

| | | | IC$_{50}$ (nM)[a] | | | | | | IC$_{90}$ (nM)[a] | | | | | |
|---|---|---|---|---|---|---|---|---|---|---|---|---|---|---|
| Virus | Clade | Tropism | T20 | C34 | D1D2Fc | 2Dm2m | 4Dm2m | 6Dm2m | T20 | C34 | D1D2Fc | 2Dm2m | 4Dm2m | 6Dm2m |
| CH64 | BC | R5 | 3.1 | 1.2 | 48 | 1.7 | 0.17 | 0.13 | 25 | 6.7 | >250 | 14 | 1.6 | 0.80 |
| CH70 | BC | R5 | 65 | 7.6 | 7.3 | 0.40 | 0.11 | 0.09 | >750 | 84 | 109 | 3.1 | 1.2 | 0.67 |
| CH91 | BC | R5 | 8.6 | 2.3 | 35 | 3.7 | 0.39 | 0.27 | 310 | 12 | >250 | 56 | 10 | 3.5 |
| CH110 | BC | R5 | 4.3 | 0.78 | 28 | 0.93 | 0.11 | 0.09 | 262 | 6.3 | >250 | 8.7 | 0.83 | 0.58 |
| CH114 | BC | R5 | 102 | 5.4 | 23 | 1.5 | 0.11 | 0.18 | >750 | 25 | 198 | 19 | 4.0 | 1.9 |
| CH117 | BC | R5 | 2.3 | 0.60 | 27 | 5.4 | 0.33 | 0.22 | 34 | 3.2 | >250 | 62 | 15 | 5.1 |
| CH119 | BC | R5 | 2.0 | 3.3 | 85 | 2.7 | 0.17 | 0.13 | 25 | 20 | >250 | 25 | 3.4 | 1.1 |
| CH120 | BC | R5 | 11 | 4.6 | 104 | 4.3 | 0.33 | 0.27 | 443 | 39 | >250 | 46 | 6.6 | 3.5 |
| CNE7 | BC | R5 | 4.3 | 6.4 | 19 | 1.5 | 0.18 | 0.14 | 58 | 22 | 161 | 8.1 | 1.8 | 1.2 |
| CNE15 | BC | R5 | 14 | 3.8 | 106 | 3.0 | 0.29 | 0.17 | 157 | 22 | >250 | 20 | 2.6 | 1.3 |
| CNE16 | BC | R5 | 14 | 11 | 11 | 0.77 | 0.08 | 0.07 | 169 | 51 | 229 | 8.5 | 1.2 | 0.71 |
| CNE20 | BC | R5 | 5.5 | 3.3 | 65 | 11 | 0.05 | 0.29 | 41 | 14 | >250 | >100 | 5.3 | 2.9 |
| CNE23 | BC | R5 | 15 | 2.1 | >250 | 5.4 | 0.49 | 0.48 | 228 | 18 | >250 | 35 | 4.9 | 9.9 |
| CNE30 | BC | R5 | 26 | 14 | 17 | 0.58 | 0.07 | 0.06 | 285 | 110 | 211 | 3.6 | 0.44 | 0.31 |
| CNE40 | BC | R5 | 4.9 | 0.77 | 0.06 | 0.04 | 0.01 | 0.01 | 108 | 7.8 | 0.50 | 0.33 | 0.11 | 0.09 |
| CNE46 | BC | R5 | 26 | 6.4 | 99 | 3.8 | 0.27 | 0.21 | 743 | 115 | >250 | 81 | 9.4 | 2.8 |
| CNE47 | BC | R5 | 4.9 | 1.9 | 152 | 1.5 | 0.11 | 0.12 | 42 | 14 | >250 | 30 | 2.8 | 1.2 |
| CNE49 | BC | R5 | 9.1 | 2.3 | 21 | 0.40 | 0.05 | 0.05 | 236 | 12 | 224 | 2.6 | 0.56 | 0.44 |
| CNE53 | BC | R5 | 51 | 2.0 | 14 | 2.8 | 0.24 | 0.47 | 721 | 23 | >250 | 95 | 5.5 | 12 |
| CNE68 | BC | R5 | 32 | 2.2 | 9.7 | 0.40 | 0.11 | 0.04 | 321 | 12 | 133 | 4.5 | 0.78 | 0.89 |
| CNE1 | B′ | X4 | 1.6 | 0.73 | 197 | 0.47 | 0.11 | 0.22 | 17 | 6.8 | >250 | 4.1 | 0.61 | 2.2 |
| CNE4 | B′ | R5 | 1.7 | 6.3 | 3.9 | 0.40 | 0.11 | 0.13 | 14 | 23 | 24 | 0.40 | 2.4 | 0.80 |
| CNE6 | B′ | R5 | 1.4 | 1.6 | 68 | 1.7 | 0.33 | 0.22 | 15 | 15 | 192 | 6.9 | 2.3 | 1.4 |
| CNE9 | B′ | R5 | 1.7 | 0.87 | 9.9 | 1.1 | 0.22 | 0.22 | 14 | 5.8 | 63 | 7.0 | 3.2 | 1.7 |
| CNE11 | B′ | R5 | 3.5 | 4.6 | >250 | 1.8 | 0.33 | 0.36 | 36 | 42 | >250 | 11 | 2.6 | 3.4 |
| CNE14 | B′ | R5 | 9.7 | 3.9 | 105 | 0.80 | 0.17 | 0.18 | 305 | 17 | 248 | 4.13 | 2.4 | 1.6 |
| CNE57 | B′ | X4 | 2.5 | 2.0 | 250 | 2.1 | 1.2 | 0.71 | 24 | 14 | >250 | >100 | 19 | 22 |
| CNE64 | B′ | R5 | 1.9 | 5.1 | 12 | 1.4 | 0.56 | 0.22 | 16 | 21 | 113 | 6.5 | 3.2 | 1.5 |
| CNE17 | C | R5 | 42 | 3.2 | 11 | 2.4 | 0.11 | 0.13 | 676 | 82 | 231 | 36 | 2.4 | 0.84 |

TABLE 7-continued

Neutralization of HIV-1 isolates predominantly circulating in China in TZM-bl cell-based assays

| Virus | Clade | Tropism | $IC_{50}$ (nM)[a] | | | | | | $IC_{90}$ (nM)[a] | | | | | |
|---|---|---|---|---|---|---|---|---|---|---|---|---|---|---|
| | | | T20 | C34 | D1D2Fc | 2Dm2m | 4Dm2m | 6Dm2m | T20 | C34 | D1D2Fc | 2Dm2m | 4Dm2m | 6Dm2m |
| CNE58 | C | R5 | 54 | 2.0 | >250 | 10 | 2.1 | 1.1 | 745 | 13 | >250 | >100 | >28 | >28 |
| CNE65 | C | R5 | 5.9 | 3.1 | 15 | 1.1 | 0.28 | 0.22 | 78 | 16 | 115 | 12 | 3.3 | 1.5 |
| CNE66 | C | R5 | 129 | 2.1 | 159 | 1.2 | 0.17 | 0.09 | 729 | 11 | >250 | >100 | 7.7 | 3.1 |
| CNE3 | AE | R5 | 5.6 | 7.1 | >250 | 1.9 | 0.39 | 0.31 | 38 | 71 | >250 | 11 | 2.8 | 2.0 |
| CNE5 | AE | R5 | 2.1 | 5.9 | 94 | 1.8 | 0.67 | 0.53 | 19 | 63 | 236 | 15 | 8.7 | 5.9 |
| CNE55 | AE | R5 | 26 | 7.9 | 213 | 5.9 | 0.45 | 0.46 | 549 | 103 | >250 | 42 | 10 | 5.1 |
| CNE59 | AE | R5 | 1.4 | 3.4 | 10 | 0.93 | 0.17 | 0.18 | 17 | 28 | 220 | 16 | 2.7 | 3.8 |
| CNE107 | AE | X4 | 3.8 | 2.8 | 135 | 3.7 | 0.52 | 0.89 | 45 | 32 | >250 | 33 | 18 | 21 |
| AE20 | AE | R5 | 212 | 7.4 | 50 | 1.5 | 0.72 | 0.49 | 572 | 69 | >250 | 10 | 5.8 | 4.1 |
| AE03 | AE | R5 | 304 | 24 | >250 | 5.7 | 0.67 | 0.40 | 510 | 85 | >250 | 58 | 12 | 15 |
| YN192.31 | AE | R5 | 42 | 27 | 155 | 5.7 | 0.89 | 2.4 | 336 | 225 | >250 | 65 | 21 | 19 |
| GX2010.36 | AE | R5 | 255 | 15 | 12 | 4.7 | 0.11 | 0.13 | >750 | 165 | >250 | 90 | 18 | 6.8 |
| Arithmetic mean[b] | | | 37 | 5.3 | 94 | 2.6 | 0.34 | 0.32 | 277 | 42 | 242 | 38 | 6.2 | 5.0 |
| Geometric mean[b] | | | 11 | 3.5 | 42 | 1.7 | 0.22 | 0.20 | 123 | 25 | 195 | 17 | 3.5 | 2.4 |

[a]The assay was performed in duplicate. Results are presented as mean without standard deviation. Means are calculated only when the difference between results for the duplicate assays was within 3-fold.
[b]Arithmetic and geometric means were calculated for all viruses including those with values >750 nM, which were assigned a value of 800, those with values >250 nM, which were assigned a value of 300, those with values >100, which were assigned a value of 150, and those with values >28 nM, which were assigned a value of 30.

TABLE 8

Binding kinetics of mD1.2 and mD1.22 to HIV-1 gp140 as measured by SPR

| HIV-1 gp140 | Clade | mD1.2 | | | mD1.22 | | |
|---|---|---|---|---|---|---|---|
| | | $K_a$ ($M^{-1} s^{-1}$) | $K_d$ ($s^{-1}$) | $K_D$ (nM) | $K_a$ ($M^{-1} s^{-1}$) | $K_d$ ($s^{-1}$) | $K_D$ (nM) |
| Gp140$_{Con-s}$ | Consensus[a] | $1.7 \times 10^5$ | $9.3 \times 10^{-4}$ | 5.4 | $1.7 \times 10^5$ | $7.7 \times 10^{-4}$ | 4.4 |
| Gp140$_{MS}$ | A | $4.2 \times 10^5$ | $1.0 \times 10^{-4}$ | 0.24 | $3.8 \times 10^5$ | $7.3 \times 10^{-5}$ | 0.19 |
| Gp140$_{89.6}$ | B | $3.4 \times 10^5$ | $4.0 \times 10^{-4}$ | 1.2 | $2.5 \times 10^5$ | $2.1 \times 10^{-4}$ | 0.87 |
| Gp140$_{CH1205442}$ | B | $1.5 \times 10^5$ | $1.1 \times 10^{-4}$ | 0.72 | $1.2 \times 10^5$ | $2.0 \times 10^{-5}$ | 0.17 |

[a]A consensus gp140 designed by aligning >1,000 sequences of HIV-1 group M.
$K_a$, association rate constant.
$K_d$, dissociation rate constant.
$K_D$, equilibrium dissociation constant.

The examples described herein demonstrate the identification of new D1 mutants. In particular, mD1.22 has improved soluble expression and stability, showed no measurable interaction with human blood B and T cell lines, and preserved binding and cross-reactivity with HIV-1 gp120. mD1.22-m36.4 fusion proteins have been shown to be potent HIV-1 neutralizers and multivalent mD1.22-m36.4 fusion proteins do not tend to enhance HIV-1 infectivity. Thus, the newly identified mutants can be used for HIV-1 prevention and therapy, and also can serve as valuable tools to study the mechanism of HIV-1 entry and biological functions of CD4 in immune responses.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition comprising
two fusion proteins each consisting essentially of SEQ ID NO: 21, and
two fusion proteins each comprising SEQ ID NO: 20,
wherein the two fusion proteins comprising SEQ ID NO: 20 are covalently bonded to each other, and
wherein one of the fusion proteins consisting essentially of SEQ ID NO: 21 is covalently bonded to one of the fusion proteins comprising SEQ ID NO: 20, and the other of the fusion proteins consisting essentially of SEQ ID NO: 21 is covalently bonded to the other of the fusion proteins comprising SEQ ID NO: 20.

2. A composition comprising the composition of claim 1 and a carrier.

3. A nucleic acid encoding each fusion protein of the composition of claim 1.

4. An isolated or purified cell comprising the nucleic acid of claim 3.

5. A conjugate comprising (a) the composition of claim 1 and (b) a cytotoxic agent.

6. A method of therapeutically inhibiting viral replication in a cell or host comprising administering to the cell or host the composition of claim 1, such that viral replication is inhibited.

7. The composition of claim 1, wherein the two fusion proteins comprising SEQ ID NO: 20 are covalently bonded to each other at the two Fc regions of each protein, the light chain constant region of one of the fusion proteins consisting essentially of SEQ ID NO: 21 is covalently bonded to the heavy chain constant region of one of the fusion proteins comprising SEQ ID NO: 20, and the light chain constant region of the other of the fusion proteins consisting essentially of SEQ ID NO: 21 is covalently bonded to the heavy chain constant region of the other of the fusion proteins comprising SEQ ID NO: 20.

8. The composition of claim 1, wherein each covalent bond is a disulfide bond.

9. The composition of claim 7, wherein each covalent bond is a disulfide bond.

10. A composition comprising
two fusion proteins each consisting essentially of SEQ ID NO: 21, and two fusion proteins each consisting essentially of SEQ ID NO: 20, wherein the two fusion proteins consisting essentially of SEQ ID NO: 20 are covalently bonded to each other, and wherein one of the fusion proteins consisting essentially of SEQ ID NO: 21 is covalently bonded to one of the fusion proteins consisting essentially of SEQ ID NO: 20, and the other of the fusion proteins consisting essentially of SEQ ID NO: 21 is covalently bonded to the other of the fusion proteins consisting essentially of SEQ ID NO: 20.

11. A composition comprising the composition of claim 10 and a carrier.

12. A nucleic acid encoding each fusion protein of the composition of claim 10.

13. An isolated or purified cell comprising the nucleic acid of claim 12.

14. A conjugate comprising (a) the composition of claim 10 and (b) a cytotoxic agent.

15. A method of therapeutically inhibiting viral replication in a cell or host comprising administering to the cell or host the composition of claim 10, such that viral replication is inhibited.

16. The composition of claim 10, wherein the two fusion proteins consisting essentially of SEQ ID NO: 20 are covalently bonded to each other at the two Fc regions of each protein, the light chain constant region of one of the fusion proteins consisting essentially of SEQ ID NO: 21 is covalently bonded to the heavy chain constant region of one of the fusion proteins consisting essentially of SEQ ID NO: 20, and the light chain constant region of the other of the fusion proteins consisting essentially of SEQ ID NO: 21 is covalently bonded to the heavy chain constant region of the other of the fusion proteins consisting essentially of SEQ ID NO: 20.

17. The composition of claim 10, wherein each covalent bond is a disulfide bond.

18. The composition of claim 16, wherein each covalent bond is a disulfide bond.

* * * * *

SEQUENCE LISTING

<160> NUMBER OF SEQ ID NOS: 23

<210> SEQ ID NO 1
<211> LENGTH: 99
<212> TYPE: PRT
<213> ORGANISM: Artificial Sequence
<220> FEATURE:
<223> OTHER INFORMATION: Synthetic

<400> SEQUENCE: 1

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly

<210> SEQ ID NO 2
<211> LENGTH: 99
<212> TYPE: PRT
<213> ORGANISM: Artificial Sequence
<220> FEATURE:
<223> OTHER INFORMATION: Synthetic

<400> SEQUENCE: 2

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asp Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly

<210> SEQ ID NO 3
<211> LENGTH: 99
<212> TYPE: PRT
<213> ORGANISM: Artificial Sequence
<220> FEATURE:
<223> OTHER INFORMATION: Synthetic

<400> SEQUENCE: 3

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

```
Gln Ile Lys Ile Leu Gly Asn Gln Gly Ser Phe Leu Thr Lys Gly Pro
         35                  40                  45

Ser Lys Leu Asn Asp Arg Ala Asp Ser Arg Arg Ser Leu Trp Asp Gln
 50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Val Gln Leu Leu
                 85                  90                  95

Val Phe Gly

<210> SEQ ID NO 4
<211> LENGTH: 99
<212> TYPE: PRT
<213> ORGANISM: Artificial Sequence
<220> FEATURE:
<223> OTHER INFORMATION: Synthetic

<400> SEQUENCE: 4

Lys Lys Val Val Tyr Gly Lys Lys Gly Asp Thr Val Glu Leu Thr Cys
 1               5                  10                  15

Thr Ala Ser Gln Lys Lys Asn Ile Gln Phe His Trp Lys Asn Ser Asn
                 20                  25                  30

Gln Ile Lys Ile Leu Gly Asn Gln Gly Ser Phe Leu Thr Lys Gly Pro
         35                  40                  45

Ser Lys Leu Asn Asp Arg Ala Asp Ser Arg Arg Ser Leu Trp Asp Gln
 50                  55                  60

Gly Asn Phe Pro Leu Ile Ile Lys Asn Leu Lys Pro Glu Asp Ser Asp
 65                  70                  75                  80

Thr Tyr Ile Cys Glu Val Glu Asp Gln Lys Glu Val Gln Leu Val
                 85                  90                  95

Val Val Gly

<210> SEQ ID NO 5
<211> LENGTH: 178
<212> TYPE: PRT
<213> ORGANISM: Artificial Sequence
<220> FEATURE:
<223> OTHER INFORMATION: Synthetic

<400> SEQUENCE: 5

Lys Lys Val Val Leu Gly Lys Lys Gly Asp Thr Val Glu Leu Thr Cys
 1               5                  10                  15

Thr Ala Ser Gln Lys Lys Ser Ile Gln Phe His Trp Lys Asn Ser Asn
                 20                  25                  30

Gln Ile Lys Ile Leu Gly Asn Gln Gly Ser Phe Leu Thr Lys Gly Pro
         35                  40                  45

Ser Lys Leu Asn Asp Arg Ala Asp Ser Arg Arg Ser Leu Trp Asp Gln
 50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Val Gln Leu Leu
                 85                  90                  95

Val Phe Gly Leu Thr Ala Asn Ser Asp Thr His Leu Leu Gln Gly Gln
             100                 105                 110

Ser Leu Thr Leu Thr Leu Glu Ser Pro Pro Gly Ser Ser Pro Ser Val
         115                 120                 125
```

```
Gln Cys Arg Ser Pro Arg Gly Lys Asn Ile Gln Gly Gly Lys Thr Leu
130                 135                 140
Ser Val Ser Gln Leu Glu Leu Gln Asp Ser Gly Thr Trp Thr Cys Thr
145                 150                 155                 160
Val Leu Gln Asn Gln Lys Lys Val Glu Phe Lys Ile Asp Ile Val Val
                165                 170                 175
Leu Ala

<210> SEQ ID NO 6
<211> LENGTH: 178
<212> TYPE: PRT
<213> ORGANISM: Artificial Sequence
<220> FEATURE:
<223> OTHER INFORMATION: Synthetic

<400> SEQUENCE: 6

Lys Lys Val Val Leu Gly Lys Lys Gly Asp Thr Val Glu Leu Thr Cys
1               5                   10                  15
Thr Ala Ser Gln Lys Lys Ser Ile Gln Phe His Trp Lys Asn Ser Asn
                20                  25                  30
Gln Ile Lys Ile Leu Gly Asn Gln Gly Ser Phe Leu Thr Lys Gly Pro
            35                  40                  45
Ser Lys Leu Asn Asp Arg Val Asp Ser Arg Arg Ser Leu Trp Asp Gln
50                  55                  60
Gly Asn Phe Pro Leu Ile Ile Lys Asn Leu Lys Ile Glu Asp Ser Asp
65                  70                  75                  80
Thr Tyr Ile Cys Glu Val Glu Asp Gln Lys Glu Glu Val Gln Leu Leu
                85                  90                  95
Val Phe Gly Leu Thr Ala Asn Ser Asp Thr His Leu Leu Gln Gly Gln
                100                 105                 110
Ser Leu Thr Leu Thr Leu Glu Ser Pro Pro Gly Ser Ser Pro Ser Val
            115                 120                 125
Gln Cys Arg Ser Pro Arg Gly Lys Asn Ile Gln Gly Gly Lys Thr Leu
130                 135                 140
Ser Val Ser Gln Leu Glu Leu Gln Asp Ser Gly Thr Trp Thr Cys Thr
145                 150                 155                 160
Val Leu Gln Asn Gln Lys Lys Val Glu Phe Lys Ile Asp Ile Val Val
                165                 170                 175
Leu Ala

<210> SEQ ID NO 7
<211> LENGTH: 227
<212> TYPE: PRT
<213> ORGANISM: Artificial Sequence
<220> FEATURE:
<223> OTHER INFORMATION: Synthetic

<400> SEQUENCE: 7

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
50                  55                  60
```

```
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 8
<211> LENGTH: 107
<212> TYPE: PRT
<213> ORGANISM: Artificial Sequence
<220> FEATURE:
<223> OTHER INFORMATION: Synthetic

<400> SEQUENCE: 8

```
Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

<210> SEQ ID NO 9
<211> LENGTH: 15
<212> TYPE: DNA
<213> ORGANISM: Artificial Sequence
<220> FEATURE:
<223> OTHER INFORMATION: Synthetic

<400> SEQUENCE: 9
ggggsggggs gggs                                                      15

```
<210> SEQ ID NO 10
<211> LENGTH: 30
<212> TYPE: DNA
<213> ORGANISM: Artificial Sequence
<220> FEATURE:
<223> OTHER INFORMATION: Synthetic

<400> SEQUENCE: 10
ggggsggggs ggggsggggs ggggsggggs                                    30

<210> SEQ ID NO 11
<211> LENGTH: 45
<212> TYPE: DNA
<213> ORGANISM: Artificial Sequence
<220> FEATURE:
<223> OTHER INFORMATION: Synthetic

<400> SEQUENCE: 11
ggggsggggs ggggsggggs ggggsggggs ggggsggggs gggges                  45

<210> SEQ ID NO 12
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (26)..(33)
<223> OTHER INFORMATION: Complementarity determining region (CDR) 1.
<220> FEATURE:
<221> NAME/KEY: MISC_FEATURE
<222> LOCATION: (51)..(58)
<223> OTHER INFORMATION: CDR2.
<220> FEATURE:
<221> NAME/KEY: MISC_FEATURE
<222> LOCATION: (96)..(106)
<223> OTHER INFORMATION: CDR3.

<400> SEQUENCE: 12
```

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Gln Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser
        115

```
<210> SEQ ID NO 13
<211> LENGTH: 117
<212> TYPE: PRT
<213> ORGANISM: Artificial Sequence
<220> FEATURE:
<223> OTHER INFORMATION: Synthetic
```

<220> FEATURE:
<221> NAME/KEY: MISC_FEATURE
<222> LOCATION: (26)..(33)
<223> OTHER INFORMATION: CDR1.
<220> FEATURE:
<221> NAME/KEY: MISC_FEATURE
<222> LOCATION: (51)..(58)
<223> OTHER INFORMATION: CDR2.
<220> FEATURE:
<221> NAME/KEY: MISC_FEATURE
<222> LOCATION: (96)..(106)
<223> OTHER INFORMATION: CDR3.

<400> SEQUENCE: 13

Gln Val Gln Leu Val Gln Ser Gly Gly Gly Leu Val Gln Pro Gly Gly
1               5                   10                  15

Ser Leu Arg Leu Ser Cys Ala Ala Ser Thr Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Asn Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser
        115

<210> SEQ ID NO 14
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (26)..(33)
<223> OTHER INFORMATION: CDR1.
<220> FEATURE:
<221> NAME/KEY: MISC_FEATURE
<222> LOCATION: (51)..(58)
<223> OTHER INFORMATION: CDR2.
<220> FEATURE:
<221> NAME/KEY: MISC_FEATURE
<222> LOCATION: (96)..(106)
<223> OTHER INFORMATION: CDR3.

<400> SEQUENCE: 14

Gln Val Gln Leu Val Gln Ser Gly Gly Gly Leu Ile Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Gln Asp Pro Gly Lys Gly Leu Glu Trp Ile
        35                  40                  45

Gly Glu Ile Asn Asp Arg Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

```
Ile Tyr Gly Gly Asn Ser Gly Gly Glu Tyr Trp Gly Gln Gly Thr Leu
            100                 105                 110

Val Thr Val Ser Ser
            115

<210> SEQ ID NO 15
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (26)..(33)
<223> OTHER INFORMATION: CDR1.
<220> FEATURE:
<221> NAME/KEY: MISC_FEATURE
<222> LOCATION: (51)..(58)
<223> OTHER INFORMATION: CDR2.
<220> FEATURE:
<221> NAME/KEY: MISC_FEATURE
<222> LOCATION: (96)..(106)
<223> OTHER INFORMATION: CDR3.

<400> SEQUENCE: 15

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
            85                  90                  95

Ile Tyr Gly Gly Asn Ser Gly Gly Glu Tyr Trp Gly Gln Gly Thr Leu
            100                 105                 110

Val Thr Val Ser Ser
            115

<210> SEQ ID NO 16
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (26)..(33)
<223> OTHER INFORMATION: CDR1.
<220> FEATURE:
<221> NAME/KEY: MISC_FEATURE
<222> LOCATION: (51)..(58)
<223> OTHER INFORMATION: CDR2.
<220> FEATURE:
<221> NAME/KEY: MISC_FEATURE
<222> LOCATION: (96)..(106)
<223> OTHER INFORMATION: CDR3.

<400> SEQUENCE: 16

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30
```

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
 50                  55                  60

Ser Arg Val Thr Ile Ser Arg Asp Asn Ser Lys Asn Thr Leu Tyr Leu
 65                  70                  75                  80

Gln Met Asn Thr Leu Ser Ala Glu Asp Thr Ala Ile Tyr Tyr Cys Ala
                 85                  90                  95

Ile Tyr Gly Gly Asn Ser Gly Gly Glu Tyr Trp Gly Gln Gly Thr Leu
            100                 105                 110

Val Thr Val Ser Ser
            115

<210> SEQ ID NO 17
<211> LENGTH: 328
<212> TYPE: PRT
<213> ORGANISM: Artificial Sequence
<220> FEATURE:
<223> OTHER INFORMATION: Synthetic

<400> SEQUENCE: 17

Lys Lys Val Val Tyr Gly Lys Lys Gly Asp Thr Val Glu Leu Thr Cys
 1               5                  10                  15

Thr Ala Ser Gln Lys Lys Asn Ile Gln Phe His Trp Lys Asn Ser Asn
                 20                  25                  30

Gln Ile Lys Ile Leu Gly Asn Gln Gly Ser Phe Leu Thr Lys Gly Pro
             35                  40                  45

Ser Lys Leu Asn Asp Arg Val Asp Ser Arg Arg Ser Leu Trp Asp Gln
 50                  55                  60

Gly Asn Phe Pro Leu Ile Ile Lys Asn Leu Lys Pro Glu Asp Ser Asp
 65                  70                  75                  80

Thr Tyr Ile Cys Glu Val Glu Asp Gln Lys Glu Glu Val Gln Leu Val
                 85                  90                  95

Val Val Gly Gly Pro Asp Lys Thr His Thr Cys Pro Pro Cys Pro Ala
            100                 105                 110

Pro Glu Leu Leu Gly Gly Pro Ser Val Phe Leu Phe Pro Pro Lys Pro
            115                 120                 125

Lys Asp Thr Leu Met Ile Ser Arg Thr Pro Glu Val Thr Cys Val Val
130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
210                 215                 220

Arg Glu Pro Gln Val Tyr Thr Leu Pro Pro Ser Arg Asp Glu Leu Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

```
Lys Thr Thr Pro Pro Val Leu Asp Ser Asp Gly Ser Phe Phe Leu Tyr
            275                 280                 285

Ser Lys Leu Thr Val Asp Lys Ser Arg Trp Gln Gln Gly Asn Val Phe
        290                 295                 300

Ser Cys Ser Val Met His Glu Ala Leu His Asn His Tyr Thr Gln Lys
305                 310                 315                 320

Ser Leu Ser Leu Ser Pro Gly Lys
                325

<210> SEQ ID NO 18
<211> LENGTH: 446
<212> TYPE: PRT
<213> ORGANISM: Artificial Sequence
<220> FEATURE:
<223> OTHER INFORMATION: Synthetci

<400> SEQUENCE: 18

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gly Gly Gly Ser Gly Gly Gly
            100                 105                 110

Gly Ser Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
        405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
435                 440                 445

<210> SEQ ID NO 19
<211> LENGTH: 239
<212> TYPE: PRT
<213> ORGANISM: Artificial Sequence
<220> FEATURE:
<223> OTHER INFORMATION: Synthetic

<400> SEQUENCE: 19

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
            85                  90                  95

Ile Tyr Gly Gly Asn Ser Gly Gly Glu Tyr Trp Gly Gln Gly Thr Leu
        100                 105                 110

Val Thr Val Ser Ser Gly Gly Gly Gly Ser Gly Gly Gly Gly Ser Gly
    115                 120                 125

Gly Gly Gly Ser Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
            165                 170                 175

Asn Ala Leu Gln Ser Gly Asn Ser Gln Glu Ser Val Thr Glu Gln Asp
        180                 185                 190

Ser Lys Asp Ser Thr Tyr Ser Leu Ser Ser Thr Leu Thr Leu Ser Lys
    195                 200                 205
```

```
Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 20
<211> LENGTH: 560
<212> TYPE: PRT
<213> ORGANISM: Artificial Sequence
<220> FEATURE:
<223> OTHER INFORMATION: Synthetic

<400> SEQUENCE: 20

```
Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gly Gly Gly Ser Gly Gly Gly
            100                 105                 110

Gly Ser Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335
```

```
Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Gly Gly
        435                 440                 445

Gly Gly Ser Gly Gly Gly Gly Ser Gly Gly Gly Gly Ser Lys Lys Val
    450                 455                 460

Val Tyr Gly Lys Lys Gly Asp Thr Val Glu Leu Thr Cys Thr Ala Ser
465                 470                 475                 480

Gln Lys Lys Asn Ile Gln Phe His Trp Lys Asn Ser Asn Gln Ile Lys
                485                 490                 495

Ile Leu Gly Asn Gln Gly Ser Phe Leu Thr Lys Gly Pro Ser Lys Leu
            500                 505                 510

Asn Asp Arg Val Asp Ser Arg Arg Ser Leu Trp Asp Gln Gly Asn Phe
        515                 520                 525

Pro Leu Ile Ile Lys Asn Leu Lys Pro Glu Asp Ser Asp Thr Tyr Ile
    530                 535                 540

Cys Glu Val Glu Asp Gln Lys Glu Glu Val Gln Leu Val Val Val Gly
545                 550                 555                 560

<210> SEQ ID NO 21
<211> LENGTH: 239
<212> TYPE: PRT
<213> ORGANISM: Artificial Sequence
<220> FEATURE:
<223> OTHER INFORMATION: Synthetic

<400> SEQUENCE: 21

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Arg Thr Val Ala Ala Pro Ser Val Phe Ile Phe Pro
    130                 135                 140
```

```
Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 22
<211> LENGTH: 560
<212> TYPE: PRT
<213> ORGANISM: Artificial Sequence
<220> FEATURE:
<223> OTHER INFORMATION: Synthetic

<400> SEQUENCE: 22

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gly Gly Gly Ser Gly Gly Gly
            100                 105                 110

Gly Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270
```

```
Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Gly Gly
        435                 440                 445

Gly Gly Ser Gly Gly Gly Ser Gly Gly Gly Ser Lys Lys Val
    450                 455                 460

Val Tyr Gly Lys Lys Gly Asp Thr Val Glu Leu Thr Cys Thr Ala Ser
465                 470                 475                 480

Gln Lys Lys Asn Ile Gln Phe His Trp Lys Asn Ser Asn Gln Ile Lys
                485                 490                 495

Ile Leu Gly Asn Gln Gly Ser Phe Leu Thr Lys Gly Pro Ser Lys Leu
            500                 505                 510

Asn Asp Arg Val Asp Ser Arg Arg Ser Leu Trp Asp Gln Gly Asn Phe
        515                 520                 525

Pro Leu Ile Ile Lys Asn Leu Lys Pro Glu Asp Ser Asp Thr Tyr Ile
    530                 535                 540

Cys Glu Val Glu Asp Gln Lys Glu Glu Val Gln Leu Val Val Val Gly
545                 550                 555                 560

<210> SEQ ID NO 23
<211> LENGTH: 353
<212> TYPE: PRT
<213> ORGANISM: Artificial Sequence
<220> FEATURE:
<223> OTHER INFORMATION: Synthetic

<400> SEQUENCE: 23

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80
```

-continued

```
Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Gly Ser Arg Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys Gly
225                 230                 235                 240

Gly Gly Gly Ser Gly Gly Gly Gly Ser Gly Gly Gly Gly Ser Lys Lys
                245                 250                 255

Val Val Tyr Gly Lys Lys Gly Asp Thr Val Glu Leu Thr Cys Thr Ala
            260                 265                 270

Ser Gln Lys Lys Asn Ile Gln Phe His Trp Lys Asn Ser Asn Gln Ile
        275                 280                 285

Lys Ile Leu Gly Asn Gln Gly Ser Phe Leu Thr Lys Gly Pro Ser Lys
        290                 295                 300

Leu Asn Asp Arg Val Asp Ser Arg Arg Ser Leu Trp Asp Gln Gly Asn
305                 310                 315                 320

Phe Pro Leu Ile Ile Lys Asn Leu Lys Pro Glu Asp Ser Asp Thr Tyr
                325                 330                 335

Ile Cys Glu Val Glu Asp Gln Lys Glu Glu Val Gln Leu Val Val Val
            340                 345                 350

Gly
```